United States Patent
Stibich et al.

(10) Patent No.: US 9,773,658 B2
(45) Date of Patent: Sep. 26, 2017

(54) ULTRAVIOLET DISCHARGE LAMP APPARATUSES HAVING LAMP HOUSINGS WHICH ARE TRANSPARENT TO ULTRAVIOLET LIGHT

(71) Applicant: Xenex Disinfection Services, LLC., San Antonio, TX (US)

(72) Inventors: Mark Andrew Stibich, Houston, TX (US); James Blaine Wolford, Chicago, IL (US); Alexander Nathan Garfield, Chicago, IL (US); Martin Rathgeber, Chicago, IL (US)

(73) Assignee: Xenex Disinfection Services, LLC., San Antonio, TX (US)

( * ) Notice: Subject to any disclaimer, the term of this patent is extended or adjusted under 35 U.S.C. 154(b) by 2 days.

(21) Appl. No.: 14/804,530

(22) Filed: Jul. 21, 2015

(65) Prior Publication Data
US 2015/0320897 A1    Nov. 12, 2015

Related U.S. Application Data

(63) Continuation of application No. 13/156,092, filed on Jun. 8, 2011, now Pat. No. 9,093,258.

(51) Int. Cl.
*H01J 61/40* (2006.01)
*G02B 5/20* (2006.01)
*A61L 2/10* (2006.01)

(52) U.S. Cl.
CPC .............. *H01J 61/40* (2013.01); *A61L 2/10* (2013.01); *G02B 5/208* (2013.01); *A61L 2202/11* (2013.01); *A61L 2202/25* (2013.01)

(58) Field of Classification Search
USPC .................. 250/504 R; 422/186.03
See application file for complete search history.

(56) References Cited

U.S. PATENT DOCUMENTS

| | | | |
|---|---|---|---|
| 2,182,732 A | 12/1939 | Meyer et al. | |
| 2,215,635 A | 9/1940 | Collins | |

(Continued)

FOREIGN PATENT DOCUMENTS

| CA | 2569130 | 6/2008 |
|---|---|---|
| CN | 87203475 | 8/1988 |

(Continued)

OTHER PUBLICATIONS

Xenex Disinfection Services, Application No. 201280038279.1; First Office Action, Sep. 25, 2015, 9 pgs.

(Continued)

*Primary Examiner* — Kiet T Nguyen
(74) *Attorney, Agent, or Firm* — Egan Peterman Enders Huston

(57) ABSTRACT

The apparatuses disclosed herein include a discharge lamp configured to emit ultraviolet and visible light, an optical filter configured to attenuate visible light, and a power circuit configured to operate the discharge lamp. Some embodiments of the apparatuses are configured such that ultraviolet light emitted from the discharge lamp and passed through the optical filter encircles an exterior surface of the apparatus. Some cases of the apparatuses include a sensor system configured to monitor a first parameter associated with the operation of the discharge lamp and a second parameter associated with the transmittance of the optical filter. Some of the apparatuses include a means for moving the optical filter while the apparatus is in operation. In some cases, the apparatuses may be configured such that the optical filter may be arranged in and out of alignment with the discharge lamp. In some embodiments, the optical filter may be a multifaceted.

18 Claims, 4 Drawing Sheets

(56) References Cited

U.S. PATENT DOCUMENTS

| | | |
|---|---|---|
| 2,382,939 A | 8/1945 | Koch |
| 2,392,095 A | 1/1946 | Lemmers |
| 2,615,120 A | 10/1952 | Macksoud |
| 3,418,069 A | 12/1968 | Eugene et al. |
| 3,949,258 A * | 4/1976 | Soodak .................. F21V 25/00 313/161 |
| 4,003,704 A | 1/1977 | Zurolo |
| 4,005,135 A | 1/1977 | Helding |
| 4,229,658 A | 10/1980 | Gonser |
| 4,877,964 A | 10/1989 | Tanaka et al. |
| 4,896,042 A | 1/1990 | Humphreys |
| 5,023,460 A | 6/1991 | Foster, Jr. et al. |
| 5,144,146 A | 9/1992 | Wekhof |
| 5,220,734 A | 6/1993 | Carver |
| 5,221,139 A | 6/1993 | Belfer |
| 5,233,723 A | 8/1993 | Hung |
| 5,251,110 A | 10/1993 | Leleve |
| 5,344,433 A | 9/1994 | Talmore |
| 5,373,430 A | 12/1994 | McDermott |
| 5,680,593 A | 10/1997 | Hiiragizawa |
| 5,689,364 A | 11/1997 | McGregor et al. |
| 5,744,094 A | 4/1998 | Castberg et al. |
| 5,768,853 A | 6/1998 | Bushnell et al. |
| 5,891,329 A | 4/1999 | Massholder |
| 5,891,399 A | 4/1999 | Owesen |
| 5,925,885 A | 7/1999 | Clark et al. |
| 6,203,060 B1 | 3/2001 | Cech et al. |
| 6,242,753 B1 | 6/2001 | Sakurai |
| 6,264,836 B1 | 7/2001 | Lantis |
| 6,398,970 B1 | 6/2002 | Justel et al. |
| 6,403,030 B1 | 6/2002 | Horton, III |
| 6,447,720 B1 | 9/2002 | Horton, III et al. |
| 6,465,799 B1 | 10/2002 | Kimble et al. |
| 6,493,087 B1 | 12/2002 | Fabinski et al. |
| 6,539,727 B1 | 4/2003 | Burnett |
| 6,566,659 B1 | 5/2003 | Clark et al. |
| 6,656,424 B1 | 12/2003 | Deal |
| 6,759,664 B2 | 7/2004 | Thompson et al. |
| 6,774,382 B2 | 8/2004 | Toshida |
| 6,897,460 B2 | 5/2005 | Kobayashi et al. |
| 6,911,177 B2 | 6/2005 | Deal |
| 6,932,494 B1 | 8/2005 | Burnett et al. |
| 6,932,903 B2 | 8/2005 | Chang |
| 6,962,239 B2 | 11/2005 | Shikai et al. |
| 6,967,008 B1 | 11/2005 | Barnes |
| 7,122,115 B2 | 10/2006 | Holt et al. |
| 7,153,808 B2 | 12/2006 | Iwamoto et al. |
| 7,175,806 B2 | 2/2007 | Deal et al. |
| 7,175,814 B2 | 2/2007 | Dionisio |
| 7,282,728 B2 | 10/2007 | Culbert |
| 7,317,393 B2 | 1/2008 | Maloney |
| 7,329,026 B1 | 2/2008 | Hayman et al. |
| 7,371,351 B2 | 5/2008 | Goswami |
| 7,380,627 B2 | 6/2008 | Huang et al. |
| 7,423,367 B2 | 9/2008 | Lantis et al. |
| 7,459,694 B2 | 12/2008 | Scheir et al. |
| 7,476,006 B2 | 1/2009 | Hinds |
| 7,498,004 B2 | 3/2009 | Saccomanno |
| 7,658,891 B1 * | 2/2010 | Barnes .................. A61L 9/015 128/205.28 |
| 7,754,156 B2 | 7/2010 | Hyde |
| 7,829,867 B2 | 11/2010 | Hlavinka et al. |
| 8,016,456 B2 | 9/2011 | Paravantsos |
| 8,021,608 B2 | 9/2011 | Skrobot et al. |
| 8,038,949 B2 | 10/2011 | Horne et al. |
| 8,142,713 B2 | 3/2012 | Gordon |
| 8,193,515 B2 | 6/2012 | Kreitenberg |
| 8,203,126 B2 | 6/2012 | Rocha-Alvarez et al. |
| 8,236,236 B2 | 8/2012 | Garner |
| 8,354,057 B2 | 1/2013 | Heselton et al. |
| 8,354,060 B2 | 1/2013 | Horne |
| 8,481,985 B2 | 7/2013 | Neister |
| 8,624,202 B2 | 1/2014 | Gil |
| 9,165,756 B2 | 10/2015 | Stibich et al. |
| 9,698,003 B2 | 7/2017 | Stibich et al. |
| 2002/0024278 A1 | 2/2002 | Matsuda et al. |
| 2002/0161418 A1 | 10/2002 | Wilkens et al. |
| 2003/0012027 A1 | 1/2003 | Hsu |
| 2003/0085631 A1 | 5/2003 | Cech et al. |
| 2003/0086821 A1 | 5/2003 | Matthews |
| 2003/0137834 A1 | 7/2003 | Jigamian et al. |
| 2003/0170152 A1 | 9/2003 | Kobayashi et al. |
| 2004/0024278 A1 | 2/2004 | Megerle |
| 2004/0052702 A1 | 3/2004 | Shuman et al. |
| 2004/0118427 A1 | 6/2004 | Palfy et al. |
| 2004/0140782 A1 | 7/2004 | Okabe et al. |
| 2004/0175290 A1 | 9/2004 | Scheir et al. |
| 2004/0202570 A1 | 10/2004 | Nadkarni |
| 2004/0244138 A1 | 12/2004 | Taylor et al. |
| 2004/0249369 A1 | 12/2004 | Muzzi et al. |
| 2005/0010331 A1 | 1/2005 | Taylor et al. |
| 2005/0025662 A1 | 2/2005 | Lestician |
| 2005/0055070 A1 | 3/2005 | Jones et al. |
| 2005/0058013 A1 | 3/2005 | Warf et al. |
| 2005/0133740 A1 | 6/2005 | Gardner |
| 2005/0151937 A1 | 7/2005 | Sugitani |
| 2005/0171636 A1 | 8/2005 | Tani |
| 2005/0186108 A1 | 8/2005 | Fields |
| 2005/0276720 A1 | 12/2005 | Correa |
| 2006/0009822 A1 | 1/2006 | Savage et al. |
| 2006/0045817 A1 | 3/2006 | Horne et al. |
| 2006/0144689 A1 | 7/2006 | Barnes et al. |
| 2006/0244403 A1 | 11/2006 | Christensson et al. |
| 2006/0252326 A1 | 11/2006 | Mishler |
| 2006/0261291 A1 | 11/2006 | Gardner |
| 2006/0284109 A1 | 12/2006 | Scheir et al. |
| 2007/0038206 A1 | 2/2007 | Altshuler et al. |
| 2007/0140893 A1 | 6/2007 | McVey et al. |
| 2007/0145292 A1 | 6/2007 | Jones |
| 2007/0188113 A1 | 8/2007 | Okamoto |
| 2007/0231189 A1 | 10/2007 | Jung et al. |
| 2007/0231193 A1 | 10/2007 | Jung et al. |
| 2007/0231204 A1 | 10/2007 | Hyde et al. |
| 2007/0253860 A1 | 11/2007 | Schroder |
| 2007/0255266 A1 | 11/2007 | Cumbie et al. |
| 2008/0056933 A1 | 3/2008 | Moore et al. |
| 2008/0085223 A1 | 4/2008 | Jung et al. |
| 2008/0112845 A1 | 5/2008 | Dunn et al. |
| 2008/0199354 A1 | 8/2008 | Gordon |
| 2008/0213128 A1 | 9/2008 | Rudy et al. |
| 2008/0253941 A1 | 10/2008 | Wichers et al. |
| 2008/0260601 A1 | 10/2008 | Lyon |
| 2008/0310996 A1 | 12/2008 | Kim et al. |
| 2009/0004047 A1 * | 1/2009 | Hunter .................. A61L 9/205 422/4 |
| 2009/0035189 A1 | 2/2009 | Wu et al. |
| 2009/0123343 A1 | 5/2009 | Kwiatkowski |
| 2009/0129974 A1 | 5/2009 | McEllen |
| 2009/0191100 A1 | 7/2009 | Deal |
| 2009/0217547 A1 | 9/2009 | Kim et al. |
| 2009/0228165 A1 | 9/2009 | Ozick et al. |
| 2009/0283120 A1 | 11/2009 | Varga et al. |
| 2009/0304553 A1 | 12/2009 | Gordon |
| 2009/0314308 A1 | 12/2009 | Kim et al. |
| 2009/0323181 A1 | 12/2009 | Andrews et al. |
| 2010/0026726 A1 | 2/2010 | Fujii et al. |
| 2010/0044319 A1 | 2/2010 | Engel et al. |
| 2010/0069898 A1 | 3/2010 | O'Neil et al. |
| 2010/0078574 A1 | 4/2010 | Cooper et al. |
| 2010/0082193 A1 | 4/2010 | Chiappetta |
| 2010/0104470 A1 | 4/2010 | McCabe |
| 2010/0111775 A1 | 5/2010 | Hyde et al. |
| 2010/0183476 A1 | 7/2010 | Lu |
| 2010/0193709 A1 | 8/2010 | Dalton |
| 2011/0002821 A1 | 1/2011 | Hyde et al. |
| 2011/0054574 A1 | 3/2011 | Felix |
| 2011/0073774 A1 | 3/2011 | Taylor et al. |
| 2011/0206554 A1 | 8/2011 | Anderle et al. |
| 2011/0215261 A1 | 9/2011 | Lyslo et al. |
| 2011/0242823 A1 | 10/2011 | Tracy et al. |
| 2012/0047763 A1 | 3/2012 | Abramovich et al. |
| 2012/0056102 A1 | 3/2012 | Stanley et al. |
| 2012/0093688 A1 | 4/2012 | Harmon et al. |
| 2012/0119108 A1 | 5/2012 | Goldshtein et al. |

(56) References Cited

U.S. PATENT DOCUMENTS

| | | |
|---|---|---|
| 2012/0126134 A1 | 5/2012 | Deal et al. |
| 2012/0223216 A1 | 9/2012 | Flaherty et al. |
| 2012/0305787 A1 | 12/2012 | Henson |
| 2012/0313532 A1 | 12/2012 | Stibich et al. |
| 2012/0315186 A1 | 12/2012 | Davis |
| 2013/0094211 A1 | 4/2013 | Drake et al. |
| 2014/0291552 A1 | 10/2014 | Schumacher |

FOREIGN PATENT DOCUMENTS

| | | |
|---|---|---|
| CN | 2117167 | 9/1992 |
| CN | 2540625 | 3/2003 |
| CN | 2678651 | 2/2005 |
| CN | 2700714 | 5/2005 |
| CN | 1715793 | 1/2006 |
| CN | 101633525 | 1/2010 |
| CN | 201439877 | 4/2010 |
| CN | 201510540 | 6/2010 |
| CN | 201558350 | 8/2010 |
| CN | 101890174 | 11/2010 |
| CN | 201755324 | 3/2011 |
| DE | 149020 | 6/1981 |
| EP | 0252571 | 1/1988 |
| EP | 0566238 | 10/1993 |
| EP | 1588720 | 10/2005 |
| EP | 2172097 | 4/2010 |
| EP | 2174670 | 4/2010 |
| EP | 2314802 | 4/2011 |
| EP | 2465543 | 6/2012 |
| GB | 637085 | 5/1950 |
| GB | 2203283 | 10/1988 |
| GB | 2452341 | 3/2009 |
| JP | 57-164062 | 10/1982 |
| JP | S61-158455 | 7/1986 |
| JP | 1125442 | 8/1989 |
| JP | H01-221166 | 9/1989 |
| JP | H05-182635 | 7/1993 |
| JP | H05284905 | 11/1993 |
| JP | 06-063107 | 3/1994 |
| JP | H06-142175 | 5/1994 |
| JP | H07-289616 | 11/1995 |
| JP | H07319080 | 12/1995 |
| JP | H08-196606 | 8/1996 |
| JP | H09161723 | 6/1997 |
| JP | H10-246468 | 9/1998 |
| JP | H11-104224 | 4/1999 |
| JP | H11-216336 | 8/1999 |
| JP | 2000217898 | 8/2000 |
| JP | 2001-340439 | 12/2001 |
| JP | 2002-000713 | 1/2002 |
| JP | 200200713 | 1/2002 |
| JP | 2002-191685 | 7/2002 |
| JP | 2002-224210 | 8/2002 |
| JP | 200227824 | 9/2002 |
| JP | 2003-135581 | 5/2003 |
| JP | 2003-262369 | 9/2003 |
| JP | 2004-073775 | 3/2004 |
| JP | 2006014964 | 1/2006 |
| JP | 2006314661 | 11/2006 |
| JP | 2009233106 | 10/2009 |
| JP | 2010-276737 | 12/2010 |
| JP | 2011-252612 | 12/2011 |
| KR | 20-0257478 | 12/2001 |
| KR | 10-2006-0097854 | 9/2006 |
| KR | 2006-0102300 | 9/2006 |
| KR | 20-2011-003951 | 4/2011 |
| RU | 2223792 | 2/2004 |
| WO | 89/03778 | 5/1989 |
| WO | 93/23730 | 11/1993 |
| WO | 9323730 | 11/1993 |
| WO | 94/06482 | 3/1994 |
| WO | 00/04430 | 1/2000 |
| WO | 01/06905 | 2/2001 |
| WO | 01-60419 | 8/2001 |
| WO | 02/058744 | 8/2002 |
| WO | 2005/082426 | 9/2005 |
| WO | 2006/070281 | 7/2006 |
| WO | 2007/001364 | 1/2007 |
| WO | 2007008879 | 1/2007 |
| WO | 2007/020282 | 2/2007 |
| WO | 2007/076359 | 7/2007 |
| WO | 2007/081401 | 7/2007 |
| WO | 2007/089312 | 8/2007 |
| WO | 2007126883 | 11/2007 |
| WO | 2008/144202 | 11/2008 |
| WO | 2010115183 | 10/2010 |
| WO | 2011/088394 | 7/2011 |
| WO | 2012040757 | 4/2012 |
| WO | 2012085250 | 6/2012 |
| WO | 2012100392 | 8/2012 |
| WO | 2012/142427 | 10/2012 |
| WO | 2014/022717 | 2/2014 |
| WO | 2014/088580 | 6/2014 |
| WO | 2014/100493 | 6/2014 |

OTHER PUBLICATIONS

Newsome, "Solaration of Short-Wave Filters," Nov. 21, 2003, pp. 1-17.
Partial International Search Report for PCT/US2012/041479 mailed Nov. 8, 2012.
International Search Report for PCT/US2012/041479 mailed May 29, 2013.
International Preliminary Report on Patentability or PCT/US2012/041479 mailed Nov. 27, 2013.
Combined Search & Examination Report for GB 1401483.1 mailed Jul. 30, 2014.
Combined Search & Examination Report for GB 1401482.3 mailed Jul. 30, 2014.
Communication for GB 1401485.6 mailed Jul. 30, 2014.
Examination Report for GB 1400090.5 mailed Aug. 18, 2014.
Search & Examination Report for GB 1401481.5 mailed Jun. 29, 2015.
Search & Examination Report for GB 1401483.1 mailed Jul. 10, 2015.
Search & Examination Report for GB 1400090.5 mailed Jul. 23, 2015.
Search & Examination Report for GB 1401485.6 mailed Sep. 23, 2015.
Search & Examination Report for GB 1513713.6 mailed Oct. 1, 2015.
Kowalski et al., "Mathematical Modeling for Ultraviolet Germicidal Irradiation for Air Disinfection," Quantitative Microbiology 2, 2000, pp. 249-270.
Kowalski et al., "Mathematical Modeling of Ultraviolet Germicidal Irradiation for Air Distribution," Quantitative Microbiology 2, 2000, pp. 249-270.
Hfmmagzine.com; Solutions, Products & Services, On Our Radar, Dec. 2010, 3 pgs.
Kenex Healthcare Services, PCT/US2012/041483; Search Report and Written Opinion; Jul. 8, 2013, 25 pgs.
Search and Examination Report; GB1515896.7; Oct. 12, 2015, 4 pgs.
Search and Examination Report; GB1400090.5; Jul. 23, 2015, 5 pgs.
Examination Report, AU2012364817; Jun. 5, 2015, 5 pgs.
Notice of the Reason for Refusal; JP2014-514868; Apr. 5, 2016, 2 pgs.
Notice of the Reason for Refusal; JP2014-514868; Feb. 21, 2017, 3 pgs.
Stibich et al., "Ultraviolet Discharge Lamp Apparatuses With One or More Reflectors", U.S. Appl. No. 13/156,131; Office Action dated Oct. 1, 2012, 14 pgs.
Stibich et al., "Ultraviolet Discharge Lamp Apparatuses With One or More Reflectors", U.S. Appl. No. 13/156,131; Office Action dated Apr. 10, 2013, 18 pgs.
Stibich et al., "Ultraviolet Discharge Lamp Apparatuses With One or More Reflectors", U.S. Appl. No. 13/156,131; Office Action dated Oct. 9, 2013, 14 pgs.

(56) References Cited

OTHER PUBLICATIONS

Stibich et al., "Ultraviolet Discharge Lamp Apparatuses With One or More Reflectors", U.S. Appl. No. 13/156,131; Office Action dated May 6, 2014, 17 pgs.
Stibich et al., "Ultraviolet Discharge Lamp Apparatuses With One or More Reflectors", U.S. Appl. No. 13/156,131; Notice of Allowance dated Jun. 5, 2015, 7 pgs.
Stibich et al., "Ultraviolet Discharge Lamp Apparatuses With One or More Reflectors", U.S. Appl. No. 14/661,089; Office Action dated Feb. 29, 2016, 63 pgs.
Stibich et al., "Ultraviolet Discharge Lamp Apparatuses With One or More Reflectors", U.S. Appl. No. 14/661,089; Office Action dated Sep. 13, 2016, 24 pgs.
Stibich et al., "Ultraviolet Discharge Lamp Apparatuses With One or More Reflectors", U.S. Appl. No. 14/661,089; Notice of Allowance dated Apr. 7, 2017, 14 pgs.
Kenex Healthcare Services, PCT/US20121041483; IPRP; Dec. 10, 2013, 16 pgs.

* cited by examiner

ULTRAVIOLET DISCHARGE LAMP APPARATUSES HAVING LAMP HOUSINGS WHICH ARE TRANSPARENT TO ULTRAVIOLET LIGHT

BACKGROUND OF THE INVENTION

1. Field of the Invention

This invention generally relates to ultraviolet discharge lamp apparatuses and, more specifically, to ultraviolet discharge lamp apparatuses having optical filters which attenuate visible light and methods of operating such apparatuses.

2. Description of the Related Art

The following descriptions and examples are not admitted to be prior art by virtue of their inclusion within this section.

Discharge lamps are used in a variety of applications to generate ultraviolet (UV) light, including but not limited to polymer curing, food sterilization, fluid and object disinfection, and room/area decontamination. For example, it is known that UV irradiation in the spectrum between approximately 200 nm and approximately 320 nm is effective in deactivating and, in some cases, killing microorganisms, giving reason to the use of ultraviolet light technology for disinfecting and/or sterilizing items. In general, discharge lamps refer to lamps which generate light by means of an internal electrical discharge between electrodes in a gas. The electrical discharge creates a plasma which supplies radiant light. In some instances, such as in mercury-vapor lamps, the light generated is continuous once the lamp is triggered. Other configurations of discharge lamps, which are often referred to as flashtubes or flashlamps, generate light for very short durations. Such discharge lamps are sometimes used to supply recurrent pulses of light and, thus, are sometimes referred to as pulsed light sources. A commonly used flashlamp is a xenon flashtube.

Although different types of discharge lamps have been investigated to provide UV light for different applications, little has been done to improve the efficiency of the ultraviolet light generated in apparatuses, particularly with respect to the propagation of the ultraviolet light (i.e., distance and angle of incidence on a target object). A reason for such a lack of advancement is that many apparatuses having discharge lamps, such as food sterilization and single object disinfection devices, are configured to treat items placed in close proximity and in direct alignment with the lamp and, thus, little or no improvement in efficiency of the UV light may be realized by altering its propagation. Furthermore, room/area decontamination systems are specifically designed to disperse light over a vast area and, thus, altering UV propagation from a system may hinder such an objective. In addition, many apparatuses with discharge lamps are limited in application and versatility. For instance, many food sterilization and single object disinfection devices are self-contained apparatuses and are configured for treatment of specific items and, thus, do not generally include features which improve the versatility of the systems for treatment for other items or use in other applications. Furthermore, some apparatuses require time consuming and/or cumbersome provisions in order to protect a user from harm. For example, pulsed ultraviolet light technology generally utilizes xenon flashlamps which generate pulses of a broad spectrum of light from deep ultraviolet to infrared, including very bright and intense visible light. Exposure of the visible light and the ultraviolet light may be harmful and, thus, provisions such as containing the pulsed light within the confines of the apparatus or shielding windows of a room in which a room decontamination unit is used may be needed.

Accordingly, it would be beneficial to develop ultraviolet discharge lamp apparatuses having features which improve their utilization, including but not limited to features which improve the efficiency of the ultraviolet light generated, increase the versatility of the apparatuses, and reduce and/or eliminate time consuming and cumbersome provisions that are required by conventional systems.

SUMMARY OF THE INVENTION

The following description of various embodiments of discharge lamp apparatuses is not to be construed in any way as limiting the subject matter of the appended claims.

The apparatuses disclosed herein include a discharge lamp configured to emit ultraviolet light and visible light, an optical filter configured to attenuate visible light, and a power circuit configured to operate the discharge lamp and are absent of optics for producing a laser from light emitted from the discharge lamp. In addition, the apparatuses may include a support structure containing the power circuit and supporting the discharge lamp. Some embodiments of the apparatuses are configured such that at least some ultraviolet light emitted from the discharge lamp and passed through the optical filter is propagated to a region which encircles an exterior surface of the apparatus and further such that the ultraviolet light propagated to the encircling region during an operation of the apparatus collectively occupies the entirety of the encircling region. Other embodiments of the apparatuses additionally or alternatively include a sensor system configured to monitor a first parameter associated with the operation of the discharge lamp and a second parameter associated with the transmittance of the optical filter. In yet other embodiments, the apparatuses additionally or alternatively include a means for moving the optical filter while the apparatus is in operation. In some cases, the apparatuses may be configured such that the optical filter may be arranged in and out of alignment with the discharge lamp. In some embodiments, the optical filter may be a multifaceted.

BRIEF DESCRIPTION OF THE DRAWINGS

Other objects and advantages of the invention will become apparent upon reading the following detailed description and upon reference to the accompanying drawings in which.

Figure 1:
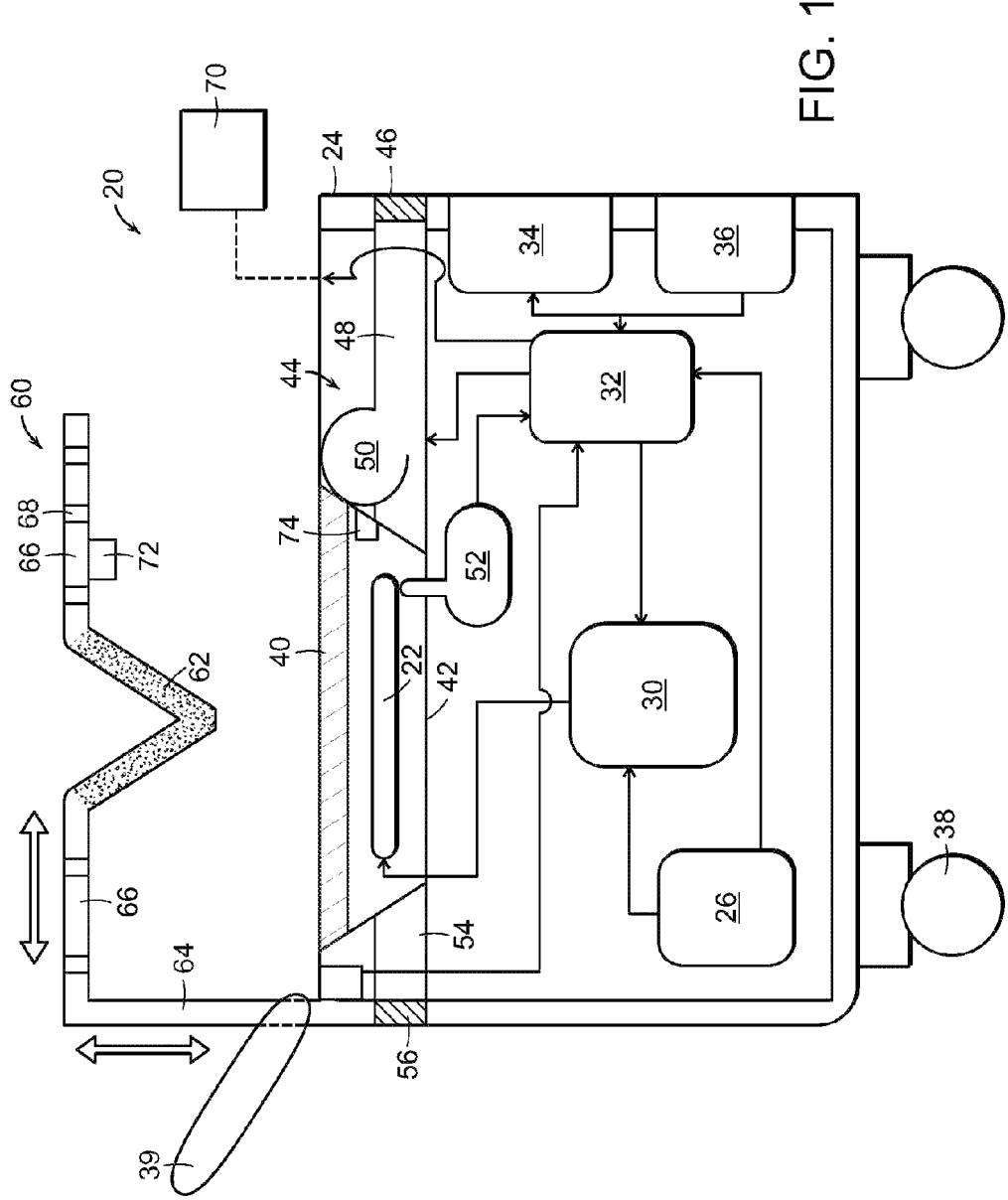
FIG. 1 is a cross-sectional schematic diagram of an ultraviolet discharge lamp apparatus having a horizontally positioned discharge lamp.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2A:
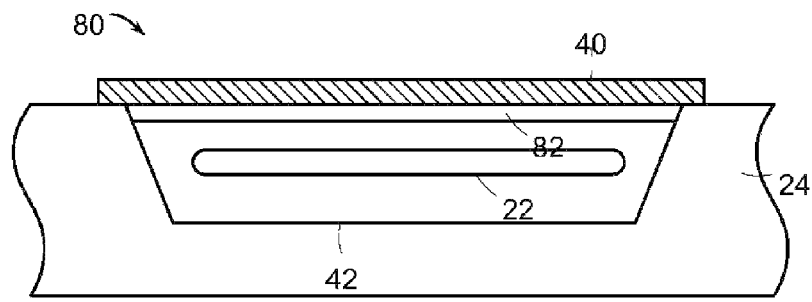
FIG. 2a depicts an alternative configuration for accommodating an optical filter in the ultraviolet discharge lamp apparatus depicted in FIG. 1.
Figure 2B:
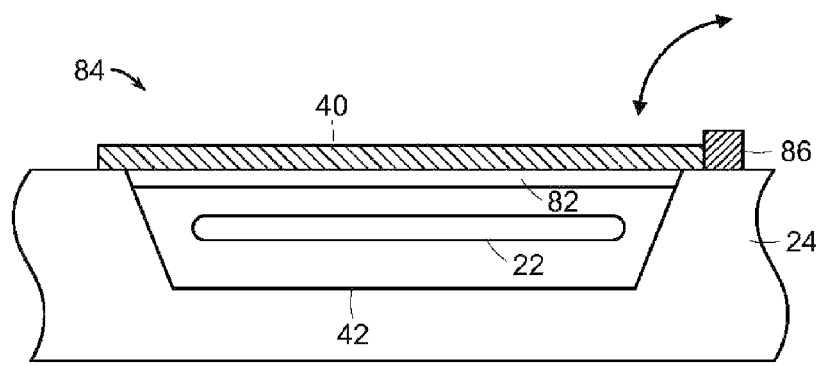
FIG. 2b depicts another alternative configuration for accommodating an optical filter in the ultraviolet discharge lamp apparatus depicted in FIG. 1.
Figure 2C:
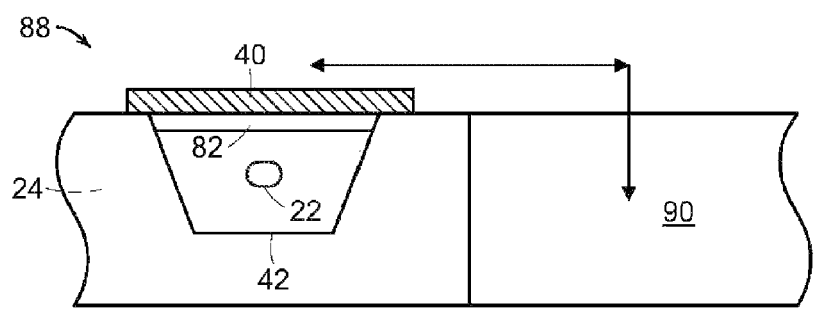
FIG. 2c depicts yet another alternative configuration for accommodating an optical filter in the ultraviolet discharge lamp apparatus depicted in FIG. 1.
Figure 3:
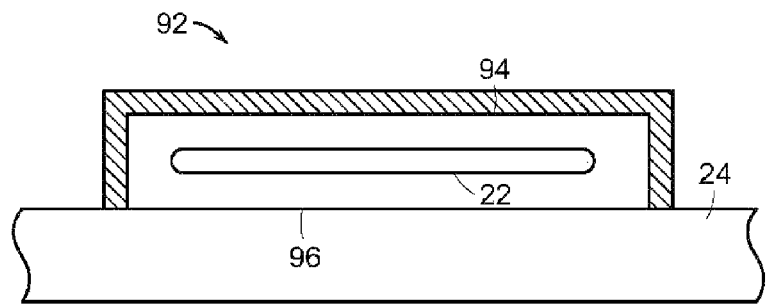
FIG. 3 depicts an alternative configuration of the ultraviolet discharge lamp apparatus depicted in FIG. 1 having a discharge lamp arranged exterior to a support structure of the apparatus.

Turning to the drawings, exemplary embodiments of discharge lamp apparatuses are provided. More specifically, exemplary configurations of apparatuses are shown in FIGS. 1-3 having a discharge lamp arranged lengthwise parallel to a plane of the apparatus at which the lamp is supported (hereinafter referred to as a "horizontally positioned lamp"). In addition, exemplary configurations of apparatuses are shown in FIGS. 4-7 having a discharge lamp arranged lengthwise perpendicular to a plane of the apparatus at which the lamp is supported (hereinafter referred to as a "vertically positioned lamp"). In addition, a system having two discharge lamp apparatuses is shown in FIG. 8. As will be set forth in more detail below, the apparatuses and features described herein are not limited to the depictions in the drawings, including that the discharge lamps are not restricted to "horizontal" and "vertical" positions. Furthermore, it is noted that the drawings are not necessarily drawn to scale in that particular features may be drawn to a larger scale than other features to emphasize their characteristics.

Each of the apparatuses described herein includes a discharge lamp configured to generate ultraviolet light and, thus, the apparatuses described herein are sometimes referred to as "ultraviolet discharge lamp apparatuses." In some embodiments, the discharge lamp of an apparatus may be further configured to generate other ranges of light, but such configurations will not deter from the reference of the apparatuses described herein as "ultraviolet discharge lamp apparatuses." In any case, the apparatuses described herein are absent of optics for producing a laser from light emitted from a discharge lamp and, accordingly, may be referred to herein as non-laser apparatuses in some embodiments. Alternatively stated, the apparatuses described herein are configured to propagate light emitted from the discharge lamp in a non-laser fashion. As set forth in more detail below, the apparatuses described herein are configured to expose areas and rooms as well as objects as a whole to ultraviolet light and, thus, are specifically configured to distribute light in a spacious manner rather than producing a narrow beam of limited diffraction as generated by lasers.

The term discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the apparatuses described herein include gas-discharge lamps as well as surface-discharge lamps. Discharge lamps may be further characterized by the type of gas/es employed and the pressure at which they are operated. The discharge lamps which may be considered for the apparatuses described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. Furthermore, the discharge lamps considered for the apparatuses described herein may be of any size and shape, depending on the design specifications of the apparatuses. Moreover, the discharge lamps considered for the apparatuses described herein may include those which generate continuous light and those which generate light in short durations, the latter of which are referred to herein as flashtubes or flashlamps. Flashtubes or flashlamps that are used to supply recurrent pulses of light are referred to herein as pulsed light sources.

A commonly used gas-discharge lamp used to produce continuous light is a mercury-vapor lamp, which may be considered for some of the apparatuses described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the apparatuses described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the apparatuses described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the apparatuses described herein to include such lamps. Rather, the aforementioned descriptions and comparisons are merely provided to offer factors which one skilled in the art may contemplate when selecting a discharge lamp for an ultraviolet discharge lamp apparatus, particularly depending on the objective and application of the apparatus.

As noted above, the apparatuses described herein are configured to distribute ultraviolet light in a spacious manner such that objects as whole and/or areas/rooms may be treated. In other words, the apparatuses described herein are not configured to produce a narrow beam of light for a specific small target as may be used for laser applications. Given their configuration to distribute ultraviolet light in a spacious manner, the apparatuses described herein may be particularly applicable for disinfecting, decontaminating and/or sterilizing objects as a whole as well as areas and/or rooms. For example, the apparatuses described herein may be used for disinfecting hospital rooms or may be used in agricultural operations, including those which are used to breed and/or farm animals. In addition or alternatively, the apparatuses described herein may be used for reducing microorganism growth on plants or sterilizing objects, such as surgical tools, food or pharmaceutical packaging. Other applications for the apparatuses described herein which involve spacious exposure to ultraviolet light may be polymer curing and medical procedures.

In some cases, the apparatuses described herein may be particularly directed to room disinfection. More specifically and as set forth in more detail below, some of the features presented for the apparatuses described herein (particularly the inclusion of an optical filter, the inclusion of a reflector system to redirect ultraviolet light propagating from a support structure of the apparatus, the adaptation to move throughout a room during operation, and/or systems including multiple discharge lamp apparatuses) may be especially suitable for room disinfection apparatuses. For this reason, many of the apparatuses described herein and depicted in the drawings are directed to room disinfection apparatuses. Furthermore, for reasons set forth below, many of the apparatuses described herein and depicted in the drawings are specifically directed to floor based freestanding portable room disinfection apparatuses. The features described with regard to the apparatuses disclosed herein, however, are not necessarily limited to room disinfection apparatuses or configurations to be floor-based, portable or freestanding. Rather, the features described herein may be applied in any type of ultraviolet discharge lamp apparatus. As used herein, the term room disinfection refers to the cleansing of a bounded area which is suitable for human occupancy so as to deactivate, destroy or prevent the growth of disease-carrying microorganisms in the area.

The room disinfection apparatuses described herein may come in a variety of configurations, including those which are floor based, wall based and ceiling based. However, although room disinfection apparatuses may be disposed within the ceiling of a room or within or against a wall, in many cases it is advantageous to position a room disinfection apparatus away from such structures. In particular, one of the primary factors affecting UV light intensity (and thus the disinfection efficiency of UV) on an object is distance to the object and, thus, in many cases it is advantageous to position a room disinfection apparatus near the center of a room or near objects suspected to be contaminated to minimize distances to objects. Moreover, in environments in which a room disinfection apparatus may be used in several rooms of a building (such as in a hospital), it is generally beneficial for the apparatus to be portable. For these reasons, many of the apparatuses described herein and depicted in the drawings are directed to freestanding, portable and floor-based room disinfection apparatuses.

In general, the apparatuses described herein may be configured to distribute light substantially uni-directionally or multi-directionally. As used herein, the phrase "configured to distribute light substantially unidirectionally" may refer to a configuration of an apparatus to propagate a majority of light emitted from a discharge lamp in a single direction with auxiliary light propagated at angles of less than 30 degrees from such a direction. All other distributions of light may be referenced for the phrase "configured to distribute light multi-directionally." Room disinfection apparatuses configured to distribute light substantially uni-directionally may be those disposed within a wall or a ceiling and/or which have a discharge lamp nested within the confines of the apparatus without an auxiliary optical component system to redirect light propagating away from the apparatus. In contrast, room disinfection apparatuses configured to distribute light multi-directionally may be those which have a discharge lamp extending out from a structure at which the discharge lamp is supported and/or which have an auxiliary optical component system to redirect light propagating away from the apparatus.

Given that a room generally includes objects of different sizes and shapes located at varying heights and distances from a given point in the room (giving rise to the number and varying location surfaces to be disinfected), it is sometimes advantageous for an apparatus used for room disinfection to be configured to distribute ultraviolet light in many directions (i.e., multi-directionally). Moreover, as noted above, it is sometimes advantageous to position a room disinfection apparatus away from room walls to reduce distances to the variety of objects in the room and effectively increase the disinfection efficiency of the UV light emitted from the apparatus. Further to such ideas, it is sometimes effective for a room disinfection apparatus to be configured such that at least some ultraviolet light generated by a discharge lamp is propagated to a region which encircles an exterior surface of the apparatus and further such that the ultraviolet light propagated to the encircling region during an operation of the apparatus collectively occupies the entirety of the encircling region. Such a configuration provides distinction from room disinfection apparatuses disposed in ceilings or walls and is described in more detail below in reference to some of the apparatuses depicted in the drawings.

Turning to FIG. 1, an exemplary configuration of an ultraviolet discharge lamp apparatus having a horizontally positioned lamp is provided. In particular, apparatus 20 is shown having discharge lamp 22 disposed within support structure 24 and specifically arranged lengthwise parallel to a plane of apparatus 20 at which discharge lamp 22 is supported (i.e., arranged parallel to an upper surface of support structure 24). As noted above and as will be set forth in more detail below, the apparatuses described herein are not restricted to embodiments in which a discharge lamp is arranged in a "horizontal position." Rather, the apparatuses described herein may include discharge lamps arranged at any angle relative to the surface plane of the support structure at which the discharge lamp is supported. Furthermore, the apparatuses described herein are not limited to embodiments in which a discharge lamp is arranged in proximity to an upper surface of an apparatus. In particular, the apparatuses described herein may have discharge lamps arranged in proximity to any exterior surface of an apparatus, including sidewalls and bottom surfaces. Horizontally positioned and vertically positioned lamps arranged in proximity to upper surfaces of support structures are discussed herein in particularity since these were the configurations used to refine some of the novel features of the apparatuses disclosed herein. However, such disclosure should not be construed to necessarily limit the arrangement of discharge lamps in the apparatuses described herein. It is further noted that the apparatuses described herein are not restricted to embodiments in which a discharge lamp is nested within the confines of a support structure as depicted in FIG. 1. Rather, apparatuses may alternatively have a discharge lamp which is arranged at least partially exterior to a support structure, such as described for the exemplary embodiments depicted in FIGS. 3-7.

In addition to discharge lamp 22, apparatus 20 includes power circuit 26 disposed within support structure 24 and circuitry connecting the power circuit to discharge lamp 22 as shown in FIG. 1. In general, power circuit 26 and the connecting circuitry are configured to operate discharge lamp 22 (i.e., to send an electrical discharge to the lamp to create a radiating plasma therein). In some cases, apparatus 20 may include additional circuitry to provide power to other features in the apparatus, including but not limited to pulse regulator circuit 30, central processing unit (CPU) 32, user interface 34 and room occupancy sensor 36 as shown in FIG. 1. Pulse regulator circuit 30 may generally be included within apparatus 20 when discharge lamp 22 is a pulsed light source. In particular, pulse regulator circuit 30 may be configured to control the frequency at which power circuit 26 applies a trigger voltage to the pulsed light source for operation. In embodiments in which discharge lamp 22 is a continuous light generation lamp, pulse regulator circuit 30 may be omitted from apparatus 20.

Although it is not necessary, one or more operations of apparatus 20 may computer-operated and, thus, apparatus 20 may, in some embodiments, include CPU 32 to carry out applicable program instructions. In addition, apparatus 20 may optionally include user interface 34 to offer a means for a user to activate operation, and possibly particular operation modes, of apparatus 20 as well as offer a means for a user to access data collected from the apparatus. Room occupancy sensor 36 is an optional safety mechanism, which may generally be configured to determine whether people are present in the room, such as by motion detection or photo recognition. Other optional features shown in apparatus 20 include wheels 38 and handle 39 to affect portability for the apparatus, but may be omitted depending on the design specifications of the apparatus.

As shown in FIG. 1, apparatus 20 may include optical filter 40, cooling system 44 and reflector system 60. As will be set forth in more detail below, the configuration of optical filters, cooling systems and reflector systems as well as the placement of discharge lamps may vary among the apparatuses described herein. In fact, alternative embodiments for one or more of such features are described in reference to FIGS. 2-7 relative to the configurations shown and described in reference to FIG. 1. Each of such embodiments include a support structure and accompanying components as described for FIG. 1, specifically in reference to support structure 22, power circuit 26, pulse regulator circuit 30, CPU 32, user interface 34, room occupancy sensor 36, wheels 38 and handle 39. Such features, however, have not been depicted in FIGS. 2-7 for simplicity purposes as well as to emphasize the differing configurations of the depicted optical filters and reflector systems as well as the placement of discharge lamps.

As noted above, each of the apparatuses described herein includes a discharge lamp configured to generate ultraviolet light. In some embodiments, a discharge lamp of an apparatus may be further configured to generate other ranges of light, such as but not limited to visible light. In some of such cases, it may be advantageous to attenuate the visible light, particularly if (but not necessarily so limited) the generated visible light is very bright and/or distracting. For instance, xenon flashlamps generate pulses of a broad spectrum of light similar to the spectrum of sunlight, but the intensity of the visible light is up to 20,000 times higher than that of sunlight. As such, the apparatuses described herein may, in some embodiments, include an optical filter configured to attenuate visible light. In some cases, the apparatuses described herein may include an optical filter configured to attenuate light in a majority portion of the visible light spectrum, greater than 75% of the visible light spectrum, or the entire visible light spectrum. In other embodiments, however, the optical filter may be configured to attenuate light in less than a majority portion of the visible light spectrum. In any case, the optical filter may be configured to attenuate a majority amount of light in a given portion of the visible light spectrum and, in some cases, greater than 75% or all light in a given portion of the visible light spectrum.

Since the apparatuses described herein are configured for ultraviolet light exposure, the optical filter must pass ultraviolet light in addition to attenuating visible light. As such, in some cases, the optical filter may be visible light bandstop filter. In other embodiments, however, the optical filter may be an ultraviolet band-pass filter. In either case, the optical filter may be configured to pass a majority amount of light in a given portion of the ultraviolet light spectrum and, in some embodiments, greater than 75% or all light in a given portion of the ultraviolet light spectrum. In some cases, the given portion of the ultraviolet light spectrum may be a majority portion of the ultraviolet light spectrum, greater than 75% of the ultraviolet light spectrum, or the entire ultraviolet light spectrum. In other embodiments, however, the given portion of the ultraviolet light spectrum may be less than a majority portion of the ultraviolet light spectrum. In some embodiments, the optical filter may be specifically configured to pass light in a specific portion of the ultraviolet spectrum. For example, in cases in which the apparatus is used for disinfection, decontamination, or sterilization purposes, the optical filter may be configured to pass light in a majority portion, greater than 75%, or the entire portion of the germicidal UV spectrum (i.e., approximately 200-320 nm). In addition or alternatively, the optical filter may be configured to pass light in a majority portion, greater than 75%, or the entire portion of the ultraviolet light spectrum known to be optimally germicidal (i.e., approximately 260-265 nm).

An exemplary optical filter glass material which may be used as an optical filter for the apparatuses described herein is Schott UG5 Glass Filter which is available from SCHOTT North America, Inc. of Elmsford, N.Y. Schott UG5 Glass Filter attenuates a majority portion of the visible light spectrum while allowing approximately 85% of ultraviolet light in a range of approximately 260 nm to approximately 265 nm to pass. Other optical filter glass materials with similar or differing characteristics may be used as well, depending on the design specifications of an apparatus. In other cases, an optical filter considered for the apparatuses described herein may be a film having any of the optical characteristics described above. In such embodiments, the film may be disposed on an optically transparent material, such as quartz. In other embodiments, an optical filter considered for the apparatuses described herein may be a combination of an optical filter glass material and a film disposed thereon, each of which is configured to attenuate visible light. The term optical filter glass material used herein refers to a material designed to influence the spectral transmission of light by either blocking or attenuating specific wavelength spectrums. In contrast, the term optically transparent used herein refers to a material which allows light to pass through without substantial blockage or attenuation of a specific wavelength spectrum. Quartz is a well known optically transparent material. The term film as used herein refers to a thin layer of a substance and is inclusive to the term coating which refers to a layer of a substance spread over a surface. Films considered for the optical filters described herein may be in solid or semi-solid form and, thus, are inclusive to solid substances and gels.

In any case, the efficiency of the optical filters in the apparatuses described herein will decrease over time due to solarization and, thus, the optical filters may need to be periodically replaced. Solarization is a phenomenon pertaining to a decrease in an optical component's ability to transmit ultraviolet radiation in relation to its time of exposure to UV radiation. In some embodiments, an optical filter considered for the apparatuses described herein may include a rate of solarization that is approximately a whole number multiple of a degradation rate of the discharge lamp. Alternatively stated, the discharge lamp may have a rate of degradation that is an approximate factor of a rate of solarization of the optical filter. The term factor in such a characterization of the optical filter refers to the mathematical definition of the term, specifically referring to a number that divides another number evenly, i.e., with no remainder. The rate of solarization of an optical filter may be approximately any whole number multiple of a degradation rate of the discharge lamp including one and, thus, in some embodiments, a rate of solarization of an optical filter may be similar or the same as the rate of degradation of a discharge lamp.

In general, discharge lamps are warrantied to a number of uses (i.e., a particular number of triggers to generate a plasma), which is determined in accordance with the expected degradation of one or more of its components. For example, pulsed light sources are often warrantied to particular number of pulses. For the apparatuses described herein, such a use count could be used to characterize a degradation rate of a discharge lamp by multiplying the amount of ultraviolet light to be emitted during each operation times the number of triggers the discharge lamp is warrantied to be used. In this manner, a degradation rate may be computed which can be correlated to a solarization rate of an optical filter. If the solarization rate of an optical filter is approximately a multiple whole number of a degradation rate of a discharge lamp in an apparatus, the components may be advantageously replaced at the same time and, thus, downtime of the apparatus may be reduced relative to embodiments in which the components are replaced based on their individual merits. In addition, in cases in which light is monitored to determine when to replace the items, the monitoring process may be simplified in that light from only one component needs to be measured. Other features addressing solarization of the optical filter incorporated in the apparatuses described herein are discussed in more detail below in reference to FIGS. 1 and 3, specifically referencing a sensor system configured to monitor parameters associated with the operation of the discharge lamp as well as the transmittance of the optical filter and also inclusion of a thermal rejuvenation system within the apparatuses.

Several different exemplary configurations and arrangements of optical filters as well as optional accompanying components are described in detail below, particularly in reference FIGS. 1-7. More specifically, several different configurations of apparatuses are described below for accommodating an optical filter in alignment with a discharge lamp. Each of optical filters in the embodiments described in reference to FIGS. 1-7 may have the optical filter characteristics set forth above. The characteristics are not reiterated for each embodiment for the sake of brevity. As noted above, although it is not necessarily so limited, an optical filter may be especially suitable for a room disinfection apparatus. This is because room disinfection apparatuses are generally configured to distribute light into the environment of the apparatus and, thus, do not include a housing to contain the light. It is noted that although the inclusion of an optical filter may be beneficial in some of the apparatuses described herein, it is not necessarily a requirement and, thus may be omitted in some embodiments.

Another distinctive feature presented for the apparatuses described herein is a reflector system configured to redirect ultraviolet light propagating away from a support structure of an apparatus. In general, the reflector systems considered for the apparatuses described herein may be used to increase the size of an area exposed to ultraviolet light by the apparatus, decrease the distance ultraviolet light is propagated to target objects or areas, and/or improve the incidence angle of ultraviolet light on target objects or areas. Several different exemplary configurations and arrangements of reflector systems configured to accomplish one or more of such objectives are described in more detail below and are shown in FIGS. 1-7. In particular, apparatuses having a repositionable reflector are described. In addition, apparatuses having a reflector system which is configured to redirect ultraviolet light propagating away from a support structure of the apparatus to encircle an exterior surface of the apparatus are described. As noted above, such a configuration may be particularly applicable for room disinfection apparatuses.

Furthermore, apparatuses are described which have a reflector system configured to redirect ultraviolet light propagating away from a support structure of an apparatus to a region exterior to the apparatus and which is between approximately 2 feet and approximately 4 feet from a floor of a room in which the apparatus is arranged. In general, the region between approximately 2 feet and approximately 4 feet from a floor of a room is considered a "high touch" region of a room since objects of frequent use are generally placed in such a region. Examples of objects typically found in a high touch zone of a room include but are not limited to desktops, keyboards, telephones, chairs, door and cabinet handles, light switches and sinks. Examples of objects in high touch zones of hospital rooms additionally or alternatively include beds, bedside tables, tray tables and intravenous stands. Due to such a region being considered a high touch zone, it is generally considered the area of highest probability to come in contact with germs and some studies indicate that the high touch zone may be the area having the highest concentration of germs. For such reasons, it may be advantageous to direct at least some ultraviolet light to a region which is between approximately 2 feet and approximately 4 feet from a floor of a room. The inclusion of a reflector system as described herein may be used to attain such an objective.

Although it is not necessarily so limited, the reflector systems described herein may be especially suitable for a room disinfection apparatus. This is because room disinfection apparatuses are generally configured to distribute light into the environment of the apparatus and, thus, do not include a housing to contain and reflect the light. For reasons set forth above, many of the apparatuses described herein and depicted in the drawings are directed to floor based room disinfection apparatuses wherein the discharge lamp is arranged to propagate light above an upper surface of the support structure of the apparatus. As noted above, such emphasized disclosure should not, however, be construed to necessarily limit the configurations of the apparatuses described herein. For instance, in embodiments in which a discharge lamp is arranged to propagate light adjacent to a sidewall surface of a support structure of an apparatus, the reflector system of the apparatus may include a reflector coupled to an uppermost portion of the sidewall surface and/or a reflector coupled to a lowermost portion of the sidewall surface such that ultraviolet light is reflected downward or upward to a concentrated area. In other cases in which a discharge lamp is arranged to propagate light below a lower surface of a support structure of an apparatus, the reflector system of the apparatus may include a reflector below the discharge lamp. Several other arrangements may be suitable as well, particularly to increase the size of an area exposed to ultraviolet light by the apparatus, decrease the distance ultraviolet light is propagated to target objects or areas, and/or improve the incidence angle of ultraviolet light on target objects or areas.

In any case, as described in more detail below, a reflector system considered for the apparatuses described herein may include one or more reflectors, which may be of any size or shape and may be arranged at any position within an apparatus to achieve the desired redirection of light. In addition, the material of the reflector/s may be any found suitable for the desired redirection of light. An exemplary reflector material found suitable for many of the apparatus configurations described herein is 4300UP Miro-UV available from ALANOD Aluminium-Veredlung GmbH & Co. KG. Another exemplary reflector material found suitable for many of the apparatus configurations described herein is GORE® DRP® Diffuse Reflector Material available from W. L. Gore & Associates, Inc. Other reflector materials may be additionally or alternatively used, depending on the design specifications of the reflection system. In any case, each of the embodiments of the reflection systems described in reference to FIGS. 1-7 may have the characteristics of the reflection systems set forth above. The characteristics are not reiterated for each embodiment the sake of brevity. As with the inclusion of an optical filter in the apparatuses described herein, although the inclusion of a reflector system may be beneficial in some apparatuses, it is not necessarily a requirement and, thus, may be omitted in some embodiments. Furthermore, the features of an optical filter and a reflector system are not mutually exclusive or mutually inclusive for an apparatus and, thus, an apparatus may include one or both features.

Turning back to FIG. 1, apparatus 20 includes optical filter 40 configured to attenuate visible light emitted from discharge lamp 22. The configuration of optical filter 40 to attenuate visible light emitted from discharge lamp 22 in FIG. 1 specifically pertains to the optical characteristics of the filter to attenuate visible light as well as the placement of the optical filter above and in alignment with discharge lamp 22. As shown in FIG. 1, optical filter 40 may be arranged flush with the upper surface of support structure 24 between the sidewalls of cup portion 42 such that optical filter 40 comprises a wall of an encasement enclosing discharge lamp 22. As described in more detail below, the apparatuses described herein include a cooling system for regulating the temperature of the discharge lamp and encasing the lamp within an enclosure offers an efficient manner to achieve a desired temperature. The use of optical filter 40 as a wall of an encasement of discharge bulb 22 may simplify the incorporation of the optical filter into apparatus 20 and, thus, may be beneficial in some design aspects. However, in some embodiments, it may be beneficial to have optical filter 40 distinct from an encasement of discharge lamp 22. For example, in some cases, it may be advantageous to be able to arrange an optical filter in and out of alignment with a discharge lamp, depending on the desired operation of the apparatus. Such a configuration is described in more detail below and exemplary variations of apparatus 20 to accommodate such a configuration are shown in FIGS. 2a-2c.

The cooling systems which may be considered for the apparatuses described herein may vary and may generally depend on the design specifications of the apparatus. Exemplary cooling systems which may be used include but are not limited to forced air systems and liquid cooling systems. Cooling system 44 shown in FIG. 1 is a forced air system including air inlet 46, air intake duct 48, fan 50, temperature sensor 52, air duct 54 and air outlet 56. In some cases, one or more of air inlet 46, air intake duct 48, air duct 54 and air outlet 56 may include air filters. In some embodiments, air duct 54 and/or air outlet 56 may additionally or alternatively include an ozone filter. In other cases, however, an ozone filter may be omitted from the apparatus. Ozone may generally be created as a byproduct from the use of discharge lamp 22, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated by the Environmental Protection Agency (EPA). It is also known that ozone is an effective germicidal agent and, thus, if the amount of ozone to be generated by a discharge lamp is lower than the EPA exposure limits for ozone, it may be beneficial to exclude an ozone filter from apparatuses including such a discharge lamp.

In any case, different configurations of outlet ducts for cooling system 44 may be considered for apparatus 20 as well as the other apparatuses described herein. For example, in some configurations, a cooling system may be configured with an air outlet on the lower portion of a sidewall of support structure 24 or on the bottom surface of support structure 24. Benefits of such alternative configurations include increased capacity for an ozone filter as well as reduced disturbance to the environment, particularly when an air outlet is positioned on the bottom surface of support structure 24. In any case, the apparatuses described herein may include a cooling system for the rest of the components within support structure 24. In some cases, the support structure cooling system may be integrated with cooling system 44 for discharge lamp 22. In other embodiments, however, the two cooling systems may be distinct.

As noted above, apparatus 20 may include reflector system 60. In general, reflector system 60 is configured to redirect ultraviolet light propagating away from support structure 24. The configuration of reflector system 60 to achieve such an objective involves the placement, shape, size and angle of reflector 62. In particular, discharge lamp 22 is arranged in apparatus 20 to propagate light above an upper surface of support structure 24, and, thus, reflector 62 is arranged above discharge lamp 22 to redirect the propagating ultraviolet light. In general, the redirection of the ultraviolet light reduces the distance ultraviolet light travels to objects adjacent to the apparatus, including underside surfaces of objects as well as top and sidewall surfaces of objects. In particular, the redirection of ultraviolet light via reflector 62 averts travel to surfaces above the apparatus (e.g., the ceiling of the room in which the apparatus is arranged) to get reflected back to objects adjacent to the apparatus. The averting of travel to surfaces above the apparatus also shortens the distance ultraviolet light needs to travel to be incident on the underside of objects (such as by via reflection from the floor of a room in which an apparatus is arranged).

In some cases, reflection system 60 may be configured to optimize the incident angle at which ultraviolet light is directed to object surfaces. For example, reflector 62 may be designed with a specific size and/or shape and/or may be repositionable such that an optimum incident angle upon an object may be obtained. Exemplary configurations in which reflector 62 is repositionable are discussed in more detail below. In any case, reflector system 60 may, in some embodiments, include one or more additional reflectors (i.e., in addition to reflector 62). For example, in some cases, reflector system 60 may include a reflector coupled to a sidewall of support structure 24, which is configured to redirect ultraviolet light received from reflector 62. The inclusion of such an additional reflector may be beneficial for directing ultraviolet light to undersides of objects within a room. Additional reflectors may be used as well or alternatively and may generally be designed (i.e., size, shape and placement) to achieve any one of the objectives noted above for reflector system 60 in conjunction with reflector 62.

In some embodiments, reflector system 60 may be specifically configured to redirect ultraviolet light propagating away from support structure 24 to a region which is between approximately 2 feet and approximately 4 feet from a floor of a room in which apparatus 20 is arranged. In particular, as set forth above, it may be advantageous to redirect ultraviolet light to such a region since it is a high touch zone. In some cases, reflector system 60 may be additionally or alternatively configured to redirect ultraviolet light propagating away from support structure 24 to a region which encircles an exterior surface of the apparatus. For instance, reflector 62 may be of a shape and size such that ultraviolet light is redirected to a region encircling support structure 24. Alternatively, reflector 62 may be of a shape and size such that ultraviolet light is redirected to a region encircling reflector system 60. In either case, a conical shape for reflector 62 may be particularly suitable to achieve such redirection.

The term encircle as used herein refers to the formation of a continuous circle around an object. The term is not restricted to embodiments of surrounding an entirety of an object or even a major portion of an object. Thus, the phrasing that the apparatuses described herein may be configured such that ultraviolet light encircles an exterior surface of an apparatus refers to the formation of a continuous ring of ultraviolet light around at least some exterior portion of the apparatus. In addition, the phrasing that the apparatuses described herein may be configured such that ultraviolet light propagated to a region encircling an apparatus during an operation of the apparatus collectively occupies the entirety of the encircling region refers to each part of a continuous ring region around an apparatus being exposed to ultraviolet light at some time during the operation of the apparatus.

Regardless of the configuration of reflection system 60 or whether apparatus 20 even includes reflection system 60, apparatus 20 may, in some embodiments, include another reflector system arranged within support structure 24 which is configured to redirect light emitted from discharge lamp 22 in the direction of light propagation away from the support structure. In particular, apparatus 20 may include a reflection system which is configured to redirect light emitted from the side and bottom surfaces of discharge lamp 22 in the same direction as the light emitted from the top surfaces of discharge lamp 22. An example of such a reflection system may involve the floor and/or sidewalls of cup portion 42 having a reflective material. Other configurations of reflection systems, however, may be considered for the apparatuses described herein.

As shown in FIG. 1, reflector system 60 may include support beams 64 and 66 to suspend reflector 62. Such a cantilever support structure is merely an example and various other support structures may be considered for reflector 62. Regardless of the configuration to suspend reflector 62 above discharge lamp 22, reflector system 60 may, in some cases, include through holes such that some light propagated toward reflector system 60 may pass through to regions above reflector system 60. An example of an embodiment is shown in FIG. 1 with support beam 66 including through holes 68. In additional or alternative cases, reflector 62 may include through holes for such a purpose. In other embodiments, reflector system 60 may be void of such through holes. Regardless, the size of reflector system 60 and, more specifically, the size of reflector 62 may vary among apparatuses. In some cases, the areal dimensions of reflector 62 may be the same or larger than the areal dimensions of the encasement in which discharge lamp 22 is contained. In this manner, nearly all the light propagating from support structure 24 will be directed to reflector 62. In other embodiments, however, the areal dimensions of reflector 62 may be smaller than the areal dimensions of the encasement in which discharge lamp 22 is contained. In such cases, some light propagating from support structure 24 may be directed beyond reflector 62.

Regardless of its size and configuration, reflector system 60 may, in some cases, be configured to move reflector 62 in the horizontal and/or vertical direction as shown by the double-arrowed lines in FIG. 1. In this manner, reflector 62 may be repositionable reflector. In some embodiments, reflector 62 may be moved between operations of apparatus 20 and, as such, reflector system 60 may, in some cases, include a means for securing the repositionable reflector at different positions within apparatus 20. In other embodiments, reflector system 60 may include a means for moving reflector 62 while apparatus 20 is in operation. The movement of reflector 62 may be continuous or periodic while apparatus 20 is in operation and, thus, reflector 62 may be moved while discharge lamp 22 is emitting light in some cases. The reference of apparatus 20 being in operation refers to when the components of the apparatus have been activated to operate discharge lamp 22 and specifically the operations by which to generate a radiating plasma within the discharge lamp. As noted above, discharge lamp 22 may, in some embodiments, be configured to generate continuous light once the lamp is triggered and, as such, the reference of apparatus 20 being in operation in such cases refers to the time used to trigger the lamp as well as the time of continuous light emission. In other embodiments, a flashlamp or a pulsed light source may be used for discharge lamp 22 and, in such cases, the reference of apparatus 20 being in operation refers to the times in which light is emitted from the lamp as well as times in between the light flashing.

In any case, a means for moving reflector 62 and sometimes securing reflector 62 at different positions within apparatus 20 may, in some embodiments, include linear actuator/s for beam 64 and/or beam 66 as well as program instructions processed by CPU 32 to affect the movement of the linear actuator/s and the timing thereof. In some embodiments, apparatus 20 may be configured such that reflector 62 may be moved manually. An exemplary means for securing reflector 62 at different positions within apparatus 20 in such cases may include notches along beam 64 and/or beam 66 and a receiving protrusion on reflector 62 or vice versa. Other various means for moving reflector 62 and/or securing reflector 62 at different positions within apparatus 20 may be considered as well and, thus, the apparatuses are not limited to the examples noted above. In any case, reflector 62 may be detachable from apparatus 20 in some cases to affect its movement relative to discharge lamp 22 and/or for ease of storage or portability of apparatus 20.

In some cases, the movement of reflector 62 may be based on characteristics of a room in which apparatus 20 is arranged. In particular, in some embodiments, it may be advantageous to analyze the characteristics of a room, such as but not limited to determining the size of the room and/or determining the number, size and/or distances of objects within the room. Such information may be worthwhile to determine a number of operational parameters for apparatus 20, such as but not limited to the placement of reflector 62 and/or the movement characteristics of reflector 62. For example, if a relatively high number of objects within a room are in the same general area, it may be beneficial to position reflector 62 to direct more light to that area as compared to other areas in the room. In some embodiments, apparatus 20 may include system 70 for collecting data regarding characteristics of a room in which the apparatus is arranged. Any system known in the art for analyzing characteristics of a room may be used. Examples include spatial sensors and/or photo recognition systems. As shown in FIG. 1, system 70 may, in some embodiments, be operationally coupled to CPU 32. In such cases, CPU 32 may be configured to retrieve data from system 70 and determine a position of reflector 62 based on the data. In some embodiments, the determined position may be relayed via user interface 34 such that a user of apparatus 20 may be informed to move reflector 62 to such a position. In other cases, CPU 32 may be configured to send a command in accordance with the determined position to a means within apparatus 20 for automatically moving reflector 62.

In some embodiments, system 70 may be additionally or alternatively used to measure doses of ultraviolet light received at an object or spot in a room in which apparatus 20 is arranged. In particular, measuring the dose of ultraviolet light received at an object or spot in a room may aid in optimizing the placement of reflector 62. As noted above, one of the primary factors affecting UV light intensity on an object is distance to the object. Another primary factor is the angle of incidence of the light. In light thereof, if doses of ultraviolet light received at an object or spot in a room can be measured, such measurements can be used to move reflector 62 such as to optimize the angle of incidence on the object or spot. Through the operational coupling of system 70 to CPU 32, CPU 32 may be configured to retrieve measurements from system 70, determine a position of reflector 62 based on the measurements, and either relay the determined position to user interface 34 and/or send a command in accordance with the determined position to a means within apparatus 20 for automatically moving reflector 62. In general, any system known in the art for measuring ultraviolet light doses may be used for system 70. Examples include ultraviolet dosimeters and radiometers.

As noted above, the efficiency of discharge lamps and optical filters will decrease over time due to solarization. In addition, discharge lamps generally have a limited life as components thereof wear after a great deal of use. As such, the apparatuses considered herein may, in some embodiments, include a sensor system configured to monitor parameter/s associated with the operation of the discharge lamp and, if applicable, parameter/s associated with the transmittance of the optical filter. In particular, such a sensor system may be beneficial for determining when to replace the discharge lamp and, if applicable, the optical filter as well as monitoring the efficiency of the UV light emitted from the apparatus since it relates to UV intensity and dose. In general, the parameter/s associated with the transmittance of an optical filter may be ultraviolet light dose or ultraviolet light intensity. The same parameters may be monitored for the operation of a discharge lamp, but pulse count may additionally or alternatively be monitored since discharge lamps are generally warrantied for a specific number of pulses. In any case, when a sensor system is to be used to monitor parameter/s associated with both the operation of a discharge lamp and the transmittance of an optical filter, the sensor system may be configured to monitor the same parameters or different parameters regarding the two components. In some embodiments, a sensor system may include a single sensor configured to measure parameter/s associated with a discharge lamp and an optical filter. In other embodiments, however, a sensor system may include distinct sensors for measuring respective parameters of a discharge lamp and an optical filter.

An exemplary sensor system for apparatus 20 of FIG. 1 includes sensor 72 arranged on the underside of reflector system 60 and sensor 74 arranged in the encasement comprising discharge lamp 22. In general, sensor 74 may be used to monitor a parameter associated with the operation of discharge lamp 22 and, more specifically, may be used to monitor light emitted from discharge lamp 22 prior to passing through optical filter 40. FIG. 1 illustrates sensor 74 disposed on a sidewall surface of cup portion 42, but sensor 74 may be arranged at any location within the encasement of discharge lamp 22. In other embodiments, sensor 74 may be omitted from apparatus 20. In particular, sensor 72 may, in some embodiments, be configured to monitor parameters associated with the operation of discharge lamp 22 (such as by pulse count) and, thus, sensor 74 may not be needed. In any case, sensor 72 may be used to monitor a parameter associated with the transmittance of optical filter 40 and, thus, may be arranged at any location on apparatus 20 or nearby apparatus 20 to receive light passed through optical filter 40. FIG. 1 shows sensor 72 arranged on the underside of reflector system 60, but such a placement is exemplary.

As noted above, it may be advantageous, in some cases, to be able to arrange an optical filter in and out of alignment with a discharge lamp, depending on the desired operation of an apparatus. Example embodiments include those in which an apparatus will be used in various rooms, some with windows and others with no windows. As noted above, it may be advantageous to have an optical filter arranged in alignment with a discharge lamp in rooms having windows. In contrast, however, it may be beneficial to be able to arrange an optical filter out of alignment with a discharge lamp in a closed room with no windows to prevent unnecessary degradation of the optical filter. More specifically, since the visible light generated by a discharge lamp in a closed room will not be seen, filtering the light may not be needed. Furthermore, as noted above, the ability of an optical filter to transmit ultraviolet radiation will decrease in relation to its time of exposure to UV radiation due to solarization. As such, having the ability to arrange an optical filter out of alignment with a discharge lamp may offer a manner in which to extend the life of an optical filter for a given apparatus.

Exemplary variations of apparatus 20 which are configured such that an optical filter may be arranged in an out of alignment with discharge lamp 22 are shown in FIGS. 2a-2c. In particular, FIGS. 2a-2c illustrate variations to the placement of optical filter 40 relative to its placement in FIG. 1 as being part of the encasement of discharge lamp 22. It is noted that FIGS. 2a-2c merely set forth examples of configurations for accommodating an optical filter in an out of alignment with a discharge lamp, but such exemplary disclosures and depictions should not be construed to limit the configurations of apparatuses described herein for such an objective. It is further noted that although FIGS. 2a-2c are described as variations to apparatus 20 in FIG. 1, FIGS. 2a-2c only depict a fraction of an apparatus in the interest to simplify the drawings. In particular, FIGS. 2a-2c only depict the placement of optical filter 40 relative to the encasement of discharge lamp 22 within support structure 24. It is noted that features depicted in FIGS. 2a-2c with the same configurations as described in reference to FIG. 1 (i.e., discharge lamp 22, support structure 24, optical filter 40 and cup portion 42) are denoted with the same reference numbers and the descriptions of such features are not reiterated for the sake of brevity. Since the embodiments of FIGS. 2a-2c do not have optical filter 40 as part of the encasement of discharge lamp 22, each of FIGS. 2a-2c include a new feature relative to FIG. 1, specifically encasement topper 82. In general, encasement topper 82 may be of an optically transparent material, such as but not limited to quartz.

As shown in FIG. 2a, variation 80 to apparatus 20 may include optical filter 40 arranged upon encasement topper 82. In such a configuration, optical filter 40 may, in some embodiments, simply be placed on top of support structure 24 (i.e., the portion of support structure 24 comprising encasement topper 82) without a means of securing optical filter 40 to the support structure. Alternatively, variation 80 may include a means to affix optical filter 40 to support structure 24. In either case, placement of optical filter 40 upon encasement topper 82 may be manual or may be automated. FIG. 2b illustrates variation 84 of apparatus 20 slightly modified relative to variation 80 in FIG. 2a. In particular, FIG. 2b illustrates the inclusion of hinge 86 mounted to one side of optical filter 40. In this manner, optical filter 40 may be arranged upon encasement topper 82 and may be removed from such a position without detachment from the apparatus. Hinge 86 may be configured to pivot optical filter 40 any angle between 90 and 180 degrees relative to the position of optical filter 40 shown in FIG. 2b. Thus, optical filter 40 may be put in any position between an upright position and a position on support structure 24 opposing discharge lamp 22 when moved from the position above the discharge lamp. Movement of optical filter 40 in such embodiments may be manual or may be automated. A different variation of apparatus 20 is depicted in FIG. 2c which has optical filter 40 arranged upon a slider for moving the optical filter in and out of alignment with discharge lamp 22 along the upper surface of support structure 24, as is indicated by the horizontal double arrow. The movement of optical filter 40 on the slider may be manual or automated.

Regardless of the configuration of apparatus 20 such that optical filter 40 may be arranged in and out of alignment with discharge lamp 22, apparatus 20 may be configured such that optical filter 40 is protected from exposure to ultraviolet light when not in alignment with discharge lamp 22. For instance, apparatus 20 may, in some embodiments, include a compartment in which optical filter 40 may be placed when it is removed from and/or repositioned in the apparatus. In addition or alternatively, apparatus 20 may include a component to cover optical filter 40 when it is taken out of alignment with discharge lamp 22. In any case, as set forth above, each of the embodiments disclosed in FIGS. 2a-2c may be automated and, thus, not only may the apparatuses disclosed herein be configured to accommodate an optical filter in and out of alignment with a discharge lamp, the apparatuses may, in some embodiments, include a means for automatically moving the optical filter in and out of alignment with the discharge lamp. Such a means may include any mechanism/s known in the art for moving objects. In some embodiments, the determination of whether to move the optical filter and/or the timing to move the optical filter may be determined by a user of apparatus 20. In other cases, however, apparatus 20 may include program instructions which are executable by CPU 32 such that the determination of whether to move the optical filter and/or the timing to move the optical filter may be automated.

In addition to such program instructions, apparatus 20 may include a system, such as system 70, for collecting data regarding characteristics of a room in which the apparatus 20 is arranged and, more specifically, for determining whether there is a window in the room. In general, any system known in the art for determining whether there is a window in the room may be used for system 70 in such cases, such as but not limited to reflection sensors. Through the operational coupling of system 70 to CPU 32, CPU 32 may be configured to retrieve data from system 70, determine a position of optical filter 40 based on the data, and either relay the determined position to user interface 34 and/or send a command in accordance with the determined position to a means within apparatus 20 for automatically moving optical filter 40. In this manner, in embodiments in which a window is detected in a room in which apparatus 20 is arranged, optical filter 40 may be arranged in alignment with discharge lamp 22 prior to operating the discharge lamp to produce light. Conversely, in embodiments in which a window is not detected in a room in which apparatus 20 is arranged, optical filter 40 may be arranged out of alignment with discharge lamp 22 prior to operating the discharge lamp to produce light. It is noted that the optional configurations of system 70 and CPU 32 to affect movement of optical filter 40 may be in addition or alternative to the configurations noted above for affecting movement of reflector 62.

FIG. 2c illustrates an optional feature for apparatus 20 in conjunction with including a slider for optical filter 40, specifically the inclusion of thermal rejuvenation chamber 90 adjacent to support structure 24. As noted above, the ability of an optical filter to transmit ultraviolet radiation will decrease in relation to its time of exposure to UV radiation due to solarization. In some cases, however, the solarization effects may be reversed if the optical filter is heated at high temperatures, such as on the order of 500° C. Although such a process may be done independent of apparatus 20, it may be advantageous in some embodiments to incorporate the process into apparatus 20 to reduce downtime of the apparatus and/or such that a replacement optical filter does not need to be on hand while optical filter 40 is being rejuvenated. Due to the high temperatures required to reverse the effects of solarization, it is preferable that thermal rejuvenation chamber 90 be a distinct chamber from support structure 24. In addition, it would be advantageous for thermal rejuvenation chamber 90 to be configured to not only withstand, but substantially contain the heat generated therein to prevent heat degradation/damage of components within support structure 24.

As shown by the downward arrow in FIG. 2c, apparatus 20 may, in some embodiments, be configured to move optical filter 40 into thermal rejuvenation chamber 90. In other embodiments, it may be done manually. In either case, the movement of optical filter 40 into thermal rejuvenation chamber 90 may, in some embodiments, be dependent on measurements taken regarding the transmittance of optical filter 40. In particular, information collected from sensor 72 regarding the transmittance of optical filter 40 may be used to determine when to move the optical filter into thermal rejuvenation chamber 90. Although the inclusion of a thermal rejuvenation chamber may be beneficial in some apparatuses, it is not a requirement and, thus, may be omitted in some embodiments. Furthermore, the features of thermal rejuvenation chamber 90 and optical filter 40 being on a slider as shown in FIG. 2c are neither mutually exclusive nor mutually inclusive for an apparatus and, thus, an apparatus may include one or both features. In fact, any of the apparatuses described herein which include an optical filter may include a thermal rejuvenation chamber, including those described above in reference to FIGS. 1, 2a and 2b as well as those described below in reference to FIGS. 3-7.

As noted above, the apparatuses described herein are not restricted to embodiments in which a discharge lamp is disposed (i.e., nested) within the confines of a support structure as depicted in FIG. 1. Rather, apparatuses may alternatively have a discharge lamp which is arranged at least partially exterior to a support structure. An exemplary embodiment of a variation to apparatus 20 in which discharge lamp 22 is arranged exterior to support structure 24 is shown in FIG. 3. As shown in FIG. 3, variation 92 may include a different optical filter configuration than that shown for apparatus 20 in FIG. 1, specifically optical filter 94 instead of optical filter 40. In addition to being configured to attenuate visible light propagated above discharge lamp 22, optical filter 94 is configured to attenuate visible light propagated sideways from discharge lamp to account for discharge lamp 22 being arranged above support structure 24. Due to such a displacement of discharge lamp 22, cup portion 42 may, in some embodiments, be omitted from support structure 24 as shown in FIG. 3. In such cases, variation 92 may, in some embodiments as shown in FIG. 3, include reflective plane 96 disposed below discharge lamp 22 to redirect light emitted from the bottom of discharge lamp 22 upward.

As further noted above, the apparatuses described herein are not restricted to embodiments in which a discharge lamp is arranged in a "horizontal position." Rather, the apparatuses described herein may include discharge lamps arranged at any angle relative to the surface plane at which the lamp is supported. Examples of apparatuses having discharge lamps arranged in a "vertical position" (i.e., arranged lengthwise perpendicular to a plane of the apparatus at which the lamp is supported) are shown in FIGS. 4-7. Each of such embodiments include a support structure, a power circuit and accompanying optional components (e.g., pulse regulator circuit, CPU, user interface, sensors, room characteristics system, hinge, slider, thermal rejuvenation chamber) as described for FIG. 1. Each of such features, however, has not been depicted in each of FIGS. 4-7 for simplicity purposes as well as to emphasize the differing configurations of the depicted optical filters and reflector systems. Furthermore, each of such features has not been described in reference to FIGS. 4-7 for the sake of brevity.

Figure 4:
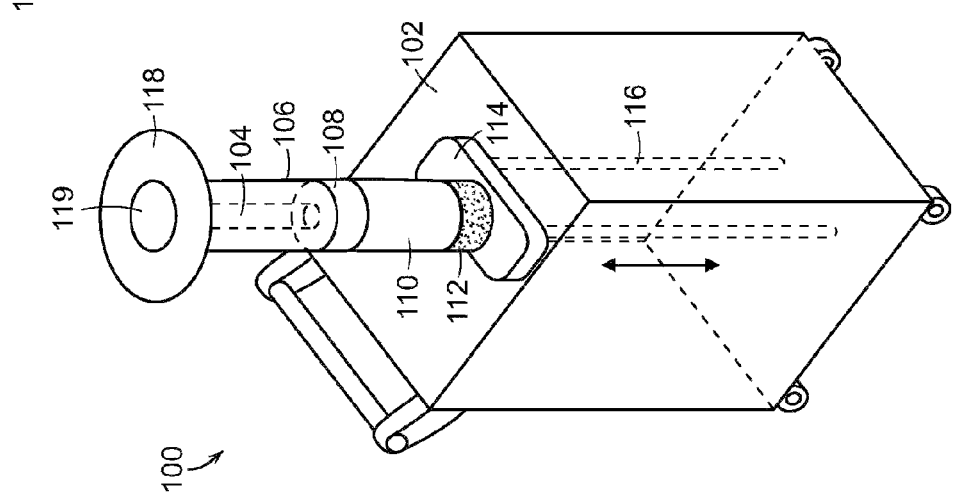
FIG. 4 an isometric drawing of an ultraviolet discharge lamp apparatus having a vertically positioned discharge lamp.

Turning to FIG. 4, apparatus 100 is shown having a discharge lamp assembly supported above support structure 102 and arranged lengthwise perpendicular to a plane of support structure 102. The discharge lamp assembly includes discharge lamp 104 surrounded by optical filter 106 and vertically disposed between fan 108 and ozone filter 119. In addition, the discharge lamp assembly includes base 110 and air filter 112 supported at base 114. Optical filter 106 may, in some embodiments, be a wall of an encasement enclosing discharge lamp 22, making up a forced air cooling system for apparatus 100 with fan 108. Apparatus 100 further includes reflector 118 affixed to ozone filter 119 at the top of optical filter 106. The characteristics of reflector 118, discharge lamp 104 and the cooling system of apparatus 100 as well as the optical characteristics of optical filter 106 may generally include those described above for all of the apparatuses considered herein and are not reiterated for the sake of brevity. As with the embodiments described above, several of the components included in apparatus 100 may be replaced and/or omitted for other configurations of apparatuses described herein, particularly optical filter 106, reflector 118 and ozone filter 119. As such, the compilation and configurations of components depicted in FIG. 4 are not necessarily mutually inclusive.

Furthermore, it is noted that apparatus 100 may include additional components (i.e., components other than what is depicted in FIG. 4). For example, in some embodiments, apparatus 100 may include an optically transparent intermediate barrier arranged between and spaced apart from discharge lamp 104 and optical filter 106. An exemplary material for the intermediate barrier may be quartz, but its composition is not so limited. The intermediate barrier may be a wall of an encasement enclosing discharge lamp 104 and, thus, may be vertically disposed between fan 108 and ozone filter 119 and part of the cooling system for apparatus 100. In such cases, optical filter 106 surrounds the intermediate barrier as a distinct glass piece spaced apart from the intermediate barrier and is secured to base 110, fan 108, and/or reflector 118. Incorporating an intermediate barrier between discharge lamp 104 and optical filter 106 may be advantageous when it is desirable to have the capability to arrange optical filter 106 in and out of alignment with discharge lamp 104 or when it is desirable to have optical filter 106 move independent of discharge lamp 104 during operation of the apparatus. In particular, an intermediate barrier may take on the role as being part of an encasement to discharge lamp 104, allowing movement of optical filter 106 without sacrificing a cooling system for discharge lamp 104.

As set forth in more detail below, it may be advantageous in some embodiments to move an optical filter of the apparatuses described herein about a central axis (e.g., to rotate or oscillate) during the operation of an apparatus. It is generally not desirable, however, to move a discharge lamp in the same manner due to concerns of damage to the discharge lamp. Thus, in some embodiments, optical filter 106 may be secured to base 110 or fan 108, but may be spaced apart from reflector 118 or vice versa. In such cases, apparatus 100 may include an additional component/s coupled to optical filter 106 which is configured to block light, particularly visible light, in the gap between optical filter 106 and base 110, fan 108 or reflector 118. Exemplary components which may be particularly suitable for such function may be a dense collection of bristles.

Figure 5:
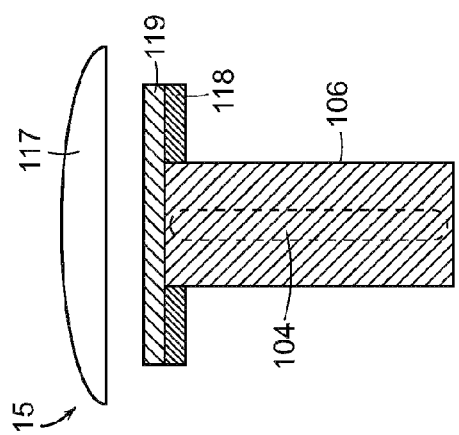
FIG. 5 depicts an alternative configuration of a discharge lamp assembly for the ultraviolet discharge lamp apparatus depicted in FIG. 4.

In any case, although the amount and rate of cooling gas discharged from an apparatus may vary greatly and may generally depend on the design specifications of the apparatus, in some embodiments the amount and rate of gas may be sufficient to trigger sprinkler systems in a room, particularly when the outlet duct of a cooling system is directed toward the ceiling as was discovered during the development of the apparatuses described herein. As such, in some cases, apparatus 100 may include a cap component spaced above the discharge lamp assembly to allow for air discharge to the side of the apparatus rather than above the apparatus. An exemplary configuration of a cap component is shown in FIG. 5 and described in more detail below. An alternative solution to prevent sprinkler systems from being triggered from exhaust of a cooling system is to lower the flow rate of gas through the lamp assembly if doing so does not cause the discharge lamp to be above its suggested maximum operating temperature. On the contrary, decreasing the gas flow rate may not be desirable in some cases (i.e., even if it does not cause the discharge lamp to exceed is maximum operating temperature) since operating discharge lamps at cooler temperatures generally offers a longer life for the lamp and theoretically generates more ultraviolet light.

FIG. 5 illustrates variation 115 to apparatus 100 having cap component 117 arranged above the lamp discharge assembly of the apparatus and, more specifically, above an outlet of the cooling system within the lamp discharge assembly such that exhaust therefrom may be directed sideways rather than above the apparatus. As shown in FIG. 5, cap component 117 may be may be domed to prevent objects from being placed thereon. Such a dome configuration is not restricted to embodiments in which an apparatus includes a cap component above a discharge lamp assembly. In particular, the top of a discharge lamp assembly may be domed in some cases to prevent objects from being placed thereon. Furthermore, the inclusion of cap component 117 is not mutually inclusive to embodiments in which ozone filter 119 comprises the entire top portion of the discharge lamp assembly as shown in FIG. 5. In particular, any of the apparatuses disclosed herein may include a component spaced apart from an outlet of its cooling system to direct exhaust therefrom.

As shown in FIG. 4, apparatus 100 may, in some embodiments, include linear actuators 116 coupled to base 114. In general, linear actuators 116 may be used to move the discharge lamp assembly and attached reflector 118 in and out of support structure 102. Such a configuration may be advantageous for protecting the discharge lamp assembly and the attached reflector from damage while apparatus 100 is not in use and, particularly, in transport. In other embodiments, linear actuators 116 may be used to move the discharge lamp assembly and the attached reflector while apparatus 100 is in operation and, in some cases, while discharge lamp 104 is emitting light. In particular, in some embodiments, it may be advantageous to move the discharge lamp assembly and the attached reflector while apparatus 100 is in operation to aid in the distribution of ultraviolet light within a room in which the apparatus is arranged. Other manners of effecting movement of the discharge lamp assembly and attached reflector may be used and, thus, the apparatuses considered herein are not necessarily limited to linear actuators 116 to achieve such an objective. For example, apparatus 100 may alternatively have fixed rails along which the discharge lamp assembly and attached reflector move. In any case, the configuration to move a discharge lamp assembly during operation of an apparatus is not exclusive to embodiments in which the apparatus includes a reflector attached to and/or above the discharge lamp assembly.

Since apparatus 100 is configured to extend discharge lamp 104 beyond an exterior surface of support structure 102, optical filter 106 is configured to surround discharge lamp 104 and, thus, may be cylindrical in shape in some cases as shown in FIG. 4. Such a configuration of optical filter 106 may include a right circular cylindrically formed optical filter glass or may include a film having the desired optical characteristics disposed upon an optically transparent right circular cylindrical substrate, such as quartz for example. Other configurations of optical filters which surround discharge lamp 104 may also be possible as described in more detail below in reference to FIGS. 6 and 7. In yet other cases, optical filter 106 may be omitted from apparatus 100. In particular, as noted above although the inclusion of an optical filter may be beneficial in some of the apparatuses described herein, it is not necessarily a requirement.

A benefit of having apparatus 100 configured to extend discharge lamp 104 beyond an exterior surface of support structure 102 is that ultraviolet light emitted from discharge lamp 104 and, if applicable, passing through optical filter 106 encircles an exterior surface of the apparatus without necessarily the inclusion of reflector 118. In particular, the extension of discharge lamp 104 beyond an exterior surface of support structure 102 innately causes ultraviolet light emitted from discharge lamp 104 and, if applicable, passing through optical filter 106 to encircle the lamp housing, which comprises an exterior surface of the apparatus. Depending on the height of support structure 102 as well as the height of the discharge lamp assembly, the extension of discharge lamp 104 beyond an exterior surface of support structure 102 may cause ultraviolet light emitted from discharge lamp 104 to encircle support structure 102 as well. Further yet, the extension of discharge lamp 104 beyond an exterior surface of support structure 102 may, in some embodiments, cause ultraviolet light to propagate to a region which is between approximately 2 feet and approximately 4 feet from a floor in which apparatus 100 is arranged, which as described above may be considered a high touch zone in a room needing particularly effective disinfection. In yet other cases, although the suspension of discharge lamp 104 above support structure 102 may be beneficial for distributing light around apparatus 100, the placement of discharge lamp 104 is not necessarily so limited. In particular, discharge lamp 104 may alternatively be arranged upon support structure 102 or may be partially disposed with support structure 102.

Since extending a discharge lamp beyond an exterior surface of a support structure is effective for propagating light around an apparatus, a reflector system for redirecting ultraviolet light propagating away from the apparatus may not be needed in some embodiments of the apparatuses described herein, particularly for apparatuses having vertically positioned discharge lamps. In some cases, however, such a reflector system may be included as shown in apparatus 100 of FIG. 4. As noted above, a reflector system of apparatus 100 may include reflector 118 affixed to ozone filter 119 at the top of optical filter 106. Although such a configuration may be advantageous for moving reflector 118 with the discharge lamp assembly (i.e., in a vertical direction in and out of support structure 102), the configuration of apparatus is not so limited. In particular, reflector 118 may alternatively be detached from the discharge lamp assembly in apparatus 100. Such a configuration may be advantageous in embodiments in which it is desirable to move the reflector independent of the discharge lamp assembly, such as for optimizing a redirection of ultraviolet light to a specific area. Other alternative configurations for apparatus 100 include reflector 118 and ozone filter 119 having the same or similar diameter and being vertically disposed relative to each other as shown in FIG. 5. In particular, FIG. 5 illustrates variation 115 to apparatus 100 in which ozone filter 119 comprises a top portion of the discharge lamp assembly with reflector 118 comprising the bottom portion of the assembly. Such a configuration may advantageously allow greater air flow through the lamp housing and, thus, provide a more efficient cooling system. In yet other embodiments, ozone filter 119 may be omitted from apparatus 100 and replaced with an air filter and/or an optical filter.

In any case, reflector 118 may be circular as shown in FIG. 4 and, may be specifically conical in some embodiments. Other shapes, however, may be considered for reflector 118. In some embodiments, reflector 118 may include holes such that some ultraviolet light may be propagated above apparatus 100. In any case, apparatus 100 may, in some embodiments, include additional reflector/s for redirecting ultraviolet light propagating from either discharge lamp 104 and/or reflector 118. For instance, in some embodiments, apparatus 100 may include a reflector disposed around the base of discharge lamp assembly. In some cases, the additional reflector may be attached to the discharge lamp assembly such that it moves with it. In other embodiments, the additional reflector may be affixed to the upper surface of support structure 102 and the discharge assembly may move through it. As with the shape of reflector 118, the additional reflector may, in some cases, be circular and even conical, but other shapes may be considered. Regardless of the configuration of reflector 118 or even its inclusion within apparatus 100, the base to which discharge lamp 104 is supported (e.g., the top of fan 108) may include a reflector.

Figure 7:
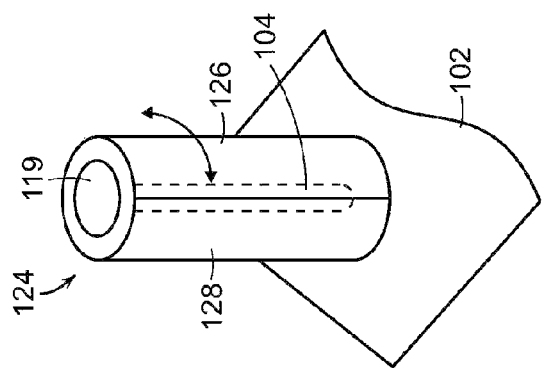
FIG. 7 depicts another alternative configuration of an optical filter for the ultraviolet discharge lamp apparatus depicted in FIG. 4.
Figure 6:
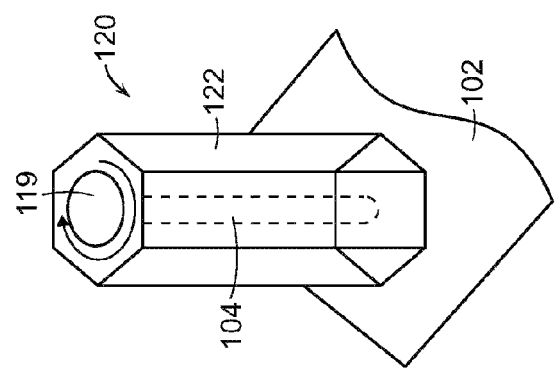
FIG. 6 depicts an alternative configuration of an optical filter for the ultraviolet discharge lamp apparatus depicted in FIG. 4.
Figure 8:
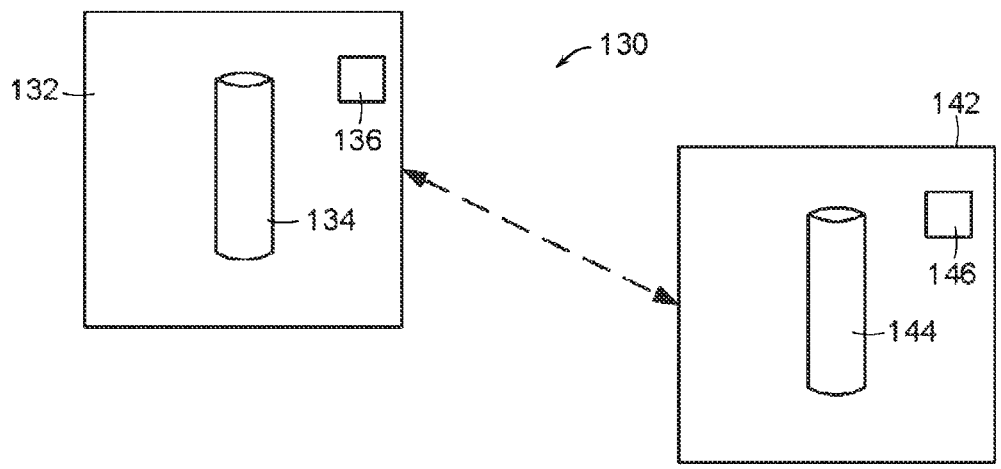
FIG. 8 depicts a system including multiple ultraviolet discharge lamp apparatuses.

As noted above, other configurations of optical filters which surround discharge lamp 104 may be considered for the apparatuses disclosed herein and are shown in FIGS. 6 and 7. It is noted that the variations of apparatuses illustrated FIGS. 6 and 7 are used to emphasize different configurations of optical filters which may be considered for the apparatuses described herein. Although not shown, the variations of apparatuses illustrated in FIGS. 6 and 7 may include any of the components shown and described in FIGS. 1-5. For example, the variations may include any components of the lamp assembly described in reference to FIG. 4 as well as reflector 118. Furthermore, the size of ozone filter 119 in FIGS. 6 and 7 may be altered from its depiction and/or ozone filter 119 may be omitted from the configurations of FIGS. 6 and 7, depending on the design specifications of an apparatus.

FIG. 6 illustrates variation 120 to apparatus 100 having multifaceted optical filter 122 surrounding discharge lamp 104. FIG. 6 illustrates multifaceted optical filter 102 arranged upon support structure 102, but such an arrangement is exemplary. Multifaceted optical filter 122 may alternatively be suspended above support structure 102 as is shown and depicted for optical filter 106 in FIG. 4. In yet other embodiments, multifaceted optical filter 122 and accompanying discharge bulb 104 may be partially disposed with support structure 122. In any case, a multifaceted optical filter generally includes multiple panels of optical filters fused together. Although multifaceted optical filter 122 is shown including six panels, it is not so limited. In particular, the multifaceted optical filters considered for the apparatuses described herein may include any plurality of optical filter panels. In addition, the optical filter panels may be made of optical filter glass material or may be made of optically transparent substrates, such as quartz for example, having films with the desired optical characteristics disposed thereon. In either case, the optical filter panels may, in some embodiments, include narrow strips of a different material (such as metal or plastic) for structural support. In some cases, one or more of the narrow support strips may partially or entirely include a reflective material to aid in redirection of light emitted from the discharge lamp around which they are arranged.

In some embodiments, a multifaceted optical filter may be cheaper than a right circular cylindrical optical filter, particularly for embodiments in which the optical filter is made of an optical filter glass material. A disadvantage of employing a multifaceted optical filter, however, may be that ultraviolet light may be blocked where the plates are fused and/or where support strips are disposed and, thus, areas of a room in which the apparatus is arranged may not be adequately disinfected. One way to overcome such deficiency is to move the multifaceted optical filter during operation of the apparatus. In particular, the multifaceted optical filter may be moved around a central axis such that ultraviolet light propagated to a region encircling apparatus 100 during the operation of the apparatus may collectively occupy the entirety of the encircling region. The multifaceted optical filter may be rotated a full revolution or more during the operation of the apparatus or may be rotated less than a revolution during the operation of an apparatus. In some embodiments, the multifaceted optical filter may be moved a fraction of a revolution, wherein the fraction corresponds to the number of optical panels comprising the multifaceted optical filter. For example, in embodiments in which the multifaceted optical filter includes six optical panels, the multifaceted optical filter may be moved ⅙ of a revolution.

In any case, some of the apparatuses described herein may include a means for moving an optical filter around a central axis. Such a means may include any mechanism known in the art for moving an object and, in further embodiments, may also include program instructions which are executable by CPU 32 such that the timing to move the optical filter around a central axis may be automated. As noted above, although it may be advantageous in some embodiments to move an optical filter of the apparatuses described herein about a central axis during the operation of an apparatus, it is generally not desirable to move a discharge lamp in the same manner due to concerns of damaging the discharge lamp. Thus, in some embodiments, variation 120 may include an intermediate barrier between discharge lamp 104 and multifaceted optical filter 122. As described above, the intermediate barrier may be part of an encasement around discharge lamp 104. In addition, multifaceted optical filter 122 may be configured to move independent of the intermediate barrier.

In yet other embodiments, multifaceted optical filter 122 may not be configured to move about a central axis during the operation of an apparatus. In particular, it is theorized that light propagated from neighboring optical filter panels of multifaceted optical filter 122 may converge at some point and, thus, ultraviolet light may encircle an exterior surface of apparatus 100 without moving multifaceted optical filter 122 around a central axis during operation of apparatus 100. In yet other embodiments, discharge lamp 104 may include a configuration which counteracts potential blocking from the fused areas of the optical filter panels and/or support strips disposed on multifaceted optical filter 122. For example, discharge lamp 104 may include a U-shaped bulb having a spacing between the "bars" of the U that is larger than the width of the fused areas and/or the support strips. In either of such cases, apparatus 100 may be referred to as being configured such that at least some of the ultraviolet light emitted from discharge lamp 104 and passed through multifaceted optical filter 122 encircles an exterior surface of the apparatus. Alternatively, it may be determined that the gaps of coverage incurred by the fused areas of the optical filter panels and/or where support strips are disposed on multifaceted optical filter 122 may not be significant and, thus, movement of multifaceted optical filter 122 may not be needed.

FIG. 7 illustrates yet another configuration of an optical filter which may be used within the apparatuses considered herein. In particular, FIG. 7 illustrates variation 124 to apparatus 100 having an assembly of optical filter 126 and reflector 128 surrounding discharge lamp 104. As shown in FIG. 7, optical filter 126 and reflector 128 may, in some embodiments, be of approximately equal size along the cylindrical sidewalls of the assembly. However, other configurations are possible, including those in which optical filter 126 is larger than the portion of reflector 128 along the sidewalls of the assembly and those in which optical filter 126 is smaller than the portion of reflector 128 along the sidewalls of the assembly. As such, a more general description of an optical filter/reflector assembly which may be considered for the apparatuses described herein may be an assembly which includes an optical filer and a reflector opposing the optical filter or vice versa.

As shown in FIG. 7, reflector 128 may, in some cases, further comprise a top portion of the assembly. Other configurations for the assembly top, however, may be considered, including optical filter 126 alternatively comprising the top portion of the assembly or having a combination of reflector 128 and optical filter 126 comprising the top portion of the assembly. It further noted that the shape of the optical filter/reflector assembly is not restricted to being a right circular cylinder as shown in FIG. 7. Rather, one or more of reflector 128 and optical filter 126 may include multiple panels and, thus, the assembly may be of a polygonal cylinder shape in some cases. In addition or alternatively, the top of the assembly may be slanted or, more generally, have a variation in height. Such a configuration may be particularly advantageous when at least a portion of the top includes reflector 128 such that ultraviolet light may be redirected downward to a desirable region within a room. In addition or alternatively, such a configuration may be advantageous for preventing exhaust from a cooling system of the apparatus from being directly routed to a ceiling of the room in which the apparatus is arranged.

In any case, the optical filter/reflector assembly of FIG. 7 may be effective for targeting a specific area within a room which is adjacent to the apparatus, such as an area having a high concentration of objects. In some embodiments, the optical filter/reflector assembly may be configured to move. For example, in some cases, the optical filter/reflector assembly may be configured to oscillate. Such a configuration may be advantageous when a given target area is larger than the span to which the optical filter/reflector assembly can effectively emit ultraviolet light when it is stationary. In other embodiments, the optical filter/reflector assembly may be configured to rotate. In any case, the movement of the optical filter/reflector assembly may, in some embodiments, be based on characteristics of a room in which apparatus 100 is arranged. In particular, if a relatively high number of objects within a room are in the same general area, it may be beneficial to position the optical filter/reflector assembly to direct light to that specific area as compared to other areas in the room. In some embodiments, apparatus 100 may include system 70 for collecting data regarding characteristics of a room in which the apparatus is arranged. Any system known in the art for analyzing characteristics of a room may be used. Examples include spatial sensors and/or photo recognition systems. In some cases, apparatus 100 may further include CPU 32 to retrieve data from system 70, determine a position of the optical filter/reflector assembly based on the data, and either relay the determined position to user interface 34 and/or send a command in accordance with the determined position to a means within apparatus 100 for automatically moving the optical filter/reflector assembly.

In addition or alternative to the features described above, the apparatuses described herein may, in some embodiments, include multiple discharge lamps. Such apparatuses may include optical filters and/or reflection systems for each discharge lamp in accordance with the descriptions of such features provided above. In some embodiments, an apparatus may include a discharge lamp with an optical filter configured to attenuate a majority amount of visible light emitted therefrom and further include a discharge lamp without an optical filter arranged in its proximity. Such a configuration may be advantageous for alternating the use of the discharge lamps depending on whether it is desired to attenuate visible light during operation of the apparatus. In any case, some or all of the multiple discharge lamps may be operated by the same power source and, if applicable, the same pulse regulator. In other embodiments, an apparatus may include a distinct power source and, if applicable, a distinct pulse regulator for each discharge lamp. It is further contemplated herein that multiple apparatuses each having one or more discharge lamps may be configured to work in communication with each other (i.e., make up a system) to disinfect a room. FIG. 8 illustrates an exemplary system 130 including multiple ultraviolet discharge lamp apparatuses 132 and 142 respectively including discharge lamp assemblies 134 and 144 and sensors 136 and 146. The dotted line between apparatuses 132 and 142 indicates that the units may be configured to communicate with each other and/or may be connected via a central processing unit.

In any case, an apparatus having multiple discharge lamps or a system having multiple discharge lamp apparatuses may be configured to operate the discharge lamps at the same time, in succession or in distinct operations of the apparatus/system. Operating multiple discharge lamps at the same time may advantageously reduce the time needed to treat an area. To further minimize the time needed to treat an area while preventing "overdosing" an area with too much UV light, an apparatus/system may be configured to modify the intensity or pulse frequency of each lamp based on characteristics of the room in which the apparatus/system is arranged or on the ultraviolet light reflected from a target object. This may involve one or more sensors, and sometimes a sensor for each discharge lamp unit, for determining characteristics of a room or the amount or intensity of ultraviolet light reflected from a target object. In some cases, an apparatus/system may include ultrasonic or other sensors to map a room in which the apparatus/system is arranged and, in some embodiments, be configured to map a room in relation to each discharge lamp unit. Such a mapping adaptation could also be included in an apparatus including a single discharge lamp which is not necessarily part of a multi-apparatus system.

In any case, a CPU of an apparatus/system may be configured to analyze the map/s and determine the necessary ultraviolet light dose in order to reach a minimum dose on all targeted surfaces. In addition, a CPU of a multi-lamp apparatus/system may be configured to allocate power to each discharge lamp unit to optimize the total treatment time for a room. The above could also be accomplished using feedback from sensors used to measure reflected ultraviolet light. Information from all sensors (e.g., ultraviolet light emitted, room size/shape, and position of all bulb units) could be fed into an equation or algorithm that determined a total operating time for each bulb unit. This would allow power to be diverted to units to optimize the decontamination speed in an area. For example, in a system configuration, two units may be used to treat different sections of an area or even different rooms. When sensors detect that one of the sections has received the required ultraviolet light dose, the corresponding unit could shut-off. The remaining unit could, in some embodiments, receive the diverted power and be able to pulse at a higher frequency if desired. The sensor system could be sophisticated enough to detect whether there was a common space between the different sections and further designate the second unit to treat the common space and therefore exclude that area from the dose calculations for the first unit. Additionally, operating time could be optimized by altering the directionality of emitted ultraviolet light for each bulb unit through changes in reflector height, orientation and/or shape.

In some embodiments, an apparatus or system could be created that moved within a room to provide multiple foci for ultraviolet light dispersal. In such cases, the information obtained through room sensing (via ultrasonic sensors or reflected ultraviolet light) could be used to guide a moving apparatus/system through a room. An apparatus/system could move using motorized wheels and have sensors to maneuver around obstacles. An apparatus/system could "learn" a room through sensing in real time as it moved, mapping the received dose on each surface as it moved. An apparatus/system could also be manually pushed through a room by a user while the apparatus/system mapped the room and then a CPU of the apparatus/system could analyze the map and determine the correct dose at each position for operation of the apparatus/system. The map and dose requirements could be used to alter the speed at which the mobile apparatus/system would pass by different surfaces.

It will be appreciated to those skilled in the art having the benefit of this disclosure that this invention is believed to provide ultraviolet discharge lamp apparatuses having optical filters which attenuate visible light and methods of operating such apparatuses. Further modifications and alternative embodiments of various aspects of the invention will be apparent to those skilled in the art in view of this description. For example, although the aforementioned discussions emphasize incorporating the optical filters within floor based room/area disinfection apparatuses, the scope of this disclosure is not so limited. In particular, the configurations of optical filters described herein may be arranged within any ultraviolet discharge lamp apparatus. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An apparatus, comprising:
a discharge lamp configured to emit ultraviolet light;
a housing encircling the discharge lamp, wherein the sidewalls of the housing are transparent to ultraviolet light, and wherein the discharge lamp and the housing are arranged in the apparatus such that ultraviolet light emitted from the discharge lamp and transmitted through the housing is projected exterior to the apparatus;
a fan disposed below the discharge lamp for drawing air into the housing; and
an ozone filter disposed above the discharge lamp, wherein the ozone filter comprises a width greater than a width of an interior cavity formed by sidewalls of the housing.

2. The apparatus of claim 1, further comprising a reflector disposed adjacent to the ozone filter exterior to and proximate an upper end of the housing to redirect light emitted from the housing downwardly.

3. The apparatus of claim 2, wherein the reflector is disposed beneath the ozone filter.

4. The apparatus of claim 2, wherein the reflector encircles the housing.

5. The apparatus of claim 1, further comprising a reflector disposed exterior to and proximate a lower end of the housing to redirect light emitted from the housing upwardly.

6. The apparatus of claim 1, further comprising a cap component arranged above the ozone filter such that exhaust discharged from the ozone filter is routed to the side of the apparatus.

7. The apparatus of claim 1, wherein an upper surface the ozone filter comprises an exterior surface of the apparatus such that exhaust discharged from the ozone filter is directed above the apparatus.

8. The apparatus of claim 1, wherein the discharge lamp is arranged lengthwise perpendicular to a horizontal plane of the apparatus.

9. The apparatus of claim 1, further comprising a temperature sensor disposed in the housing.

10. An apparatus, comprising:
a discharge lamp configured to emit ultraviolet light;
a housing encircling the discharge lamp, wherein the sidewalls of the housing are transparent to ultraviolet light, and wherein the discharge lamp and the housing are arranged in the apparatus such that ultraviolet light emitted from the discharge lamp and transmitted through the housing is projected exterior to the apparatus;
a gas inlet disposed at a lower end of the housing;
a gas outlet disposed at an upper end of the housing;
a cap component disposed above the gas outlet to redirect exhaust discharged from the gas outlet to a side of the apparatus; and
a reflector disposed below the cap component exterior to and proximate the upper end of the housing to redirect light emitted from the housing downwardly.

11. The apparatus of claim 10, wherein the reflector is disposed below a region at which the redirected exhaust is discharged from the apparatus.

12. The apparatus of claim 10, further comprising an ozone filter disposed near the gas outlet above the discharge lamp.

13. The apparatus of claim 12, wherein the ozone filter comprises a width substantially similar to a width of an interior cavity formed by sidewalls of the housing encircling the discharge lamp.

14. The apparatus of claim 12, wherein the ozone filter comprises a width greater than a width of an interior cavity formed by sidewalls of the housing encircling the discharge lamp.

15. The apparatus of claim 12, wherein the reflector is disposed beneath the ozone filter.

16. The apparatus of claim 12, wherein the reflector encircles the ozone filter.

17. The apparatus of claim 10, wherein the discharge lamp is arranged lengthwise perpendicular to a horizontal plane of the apparatus.

18. The apparatus of claim 10, further comprising a temperature sensor disposed in the housing.

* * * * *